(12) United States Patent
Houriet, Jr. et al.

(10) Patent No.: US 7,921,125 B1
(45) Date of Patent: Apr. 5, 2011

(54) VIRTUAL DATA ROOM WITH ACCESS TO CLINICAL TRIAL STATUS REPORTS BASED ON REAL-TIME CLINICAL TRIAL DATA

(75) Inventors: John W. Houriet, Jr., Yardley, PA (US); Ambalavanan Subbiah, Monmouth Junction, NJ (US); Mario A. Paes, Marlton, NJ (US)

(73) Assignee: Numoda Technologies, Inc., Philadelphia, PA (US)

( * ) Notice: Subject to any disclaimer, the term of this patent is extended or adjusted under 35 U.S.C. 154(b) by 0 days.

(21) Appl. No.: 12/898,369

(22) Filed: Oct. 5, 2010

Related U.S. Application Data

(60) Provisional application No. 61/365,904, filed on Jul. 20, 2010.

(51) Int. Cl.
G06F 7/00 (2006.01)
G06F 17/30 (2006.01)

(52) U.S. Cl. .................. 707/754; 707/783; 707/941

(58) Field of Classification Search .................. 707/704, 707/754, 783, 941, 999.008, 999.009, 999.107
See application file for complete search history.

(56) References Cited

U.S. PATENT DOCUMENTS

| 7,054,823 | B1 | 5/2006 | Briegs et al. | |
|---|---|---|---|---|
| 7,457,765 | B2 * | 11/2008 | Thompson et al. | 705/9 |
| 7,657,446 | B1 | 2/2010 | Houriet, Jr. et al. | |
| 7,752,057 | B2 | 7/2010 | Ikeguchi et al. | |
| 2003/0208378 | A1 | 11/2003 | Thangaraj et al. | |
| 2004/0093240 | A1 | 5/2004 | Shah | |
| 2004/0152056 | A1 | 8/2004 | Lamb et al. | |
| 2004/0181679 | A1 * | 9/2004 | Dettinger et al. | 713/193 |
| 2005/0055241 | A1 | 3/2005 | Horstmann | |
| 2005/0075832 | A1 | 4/2005 | Ikeguchi et al. | |
| 2005/0080721 | A1 | 4/2005 | Kearney et al. | |
| 2005/0131740 | A1 * | 6/2005 | Massenzio et al. | 705/2 |
| 2006/0129326 | A1 | 6/2006 | Braconnier et al. | |
| 2010/0228699 | A1 | 9/2010 | Webber et al. | |

FOREIGN PATENT DOCUMENTS
WO 2010071802 A2 6/2010

OTHER PUBLICATIONS

Mark D. Uehling, "Clinical Trial Data Management: Tortured by Paper," Aug. 13, 2002, printout from web address: http://www.bio-itworld.com/archive/081302/tortured/html, 6 pages.

Sacha Pfeiffer, "The data room," The Boston Globe, Jan. 23, 2006, 4 pages.

(Continued)

*Primary Examiner* — James Trujillo
*Assistant Examiner* — Marc Somers
(74) *Attorney, Agent, or Firm* — Panitch Schwarze Belisario & Nadel LLP

(57) ABSTRACT

A virtual data room distributes information associated with an investigational product, such as an investigational compound. The information includes documents associated with the investigational product; and reports based on live clinical study data of the investigational product. The live clinical study data includes cleaned and not cleaned data records. For a designated subset of data records, the reports use data associated with only cleaned data records, and for the remaining data records, the reports use data regardless of whether the data is associated with cleaned or not cleaned data records.

20 Claims, 51 Drawing Sheets

OTHER PUBLICATIONS

Virtual Data Room, VENUE. RR Donnelley & Sons Company, printout from web address: http://www.rrdonnelley.com/wwwFinancial/CapitalMarkets/Solutions/venue_virtualdataroom_lifesciences.asp, printout date: Sep. 13, 2010, original posting date: unknown, 3 pages.

VENUE, RR Donnelley & Sons Company, printout from web address: http://www.venue.rrd.com/wwwVenue/Solutions/Life-Sciences.asp, printout date: Nov. 16, 2009, original posting date: unknown, 2 pages.

John Postle, "Using SharePoint in a Regulated Environment." Life Science Leader, Jul. 2009, printout from web address: http://www.lifescienceleader.com/index.php?option=com_jambozine&layout=article&view=page&aid=3851, 3 pages.

Pandesa ShareVault for Pharmaceutical Partnering, printout from web address: http://www.sharevault.com/solutions/pharmalicensing.htm, printout date: Jul. 2, 2010, original posting date: unknown, 2 pages.

"Pandesa ShareVault Enables Secure, Real-time Due Diligence for Biopharmaceutical Partnering," News release, Sep. 16, 2009, printout from web address: http://www.prweb.com/printer/2887304.htm, 2 pages.

Michael Ball et al. "Using the Web to manage clinical trials," Innovations in Pharmaceutical Technology, 96-100, Phase Forward Inc., Dec. 2001, 4 pages.

"Accelerate Your Clinical Trials," Intralinks for Life Sciences, Copyright © 2009 IntraLinks, Inc., printout from web address: http://www.intralinks.com/life-sciences-clinical-studies/, 2 pages.

"Managing the Business and Potential Opportunities," IntraLinks® product brochure, Copyright © 2009 IntraLinks, Inc., 2 pages.

"Cost-Effective Document Management Solutions for Business-Critical Processes," IntraLinks® White Paper, Copyright © 2008 THINKstrategies, Inc., printout from web address: http://www.intralinks.com/articles/wp-saas-intralinks-p2.pdf, 9 pages.

Jens Backbom, "CSCW and the Enterprise: The Development of an eCollaboration Strategy at AstraZeneca Pharmaceuticals," Master of Science Thesis, Stockholm, Sweden 2008, printout from web address: http://www.collaboratesimply.com/images/Avanade_DigitalCollaboration.pdf, 56 pages.

"Anatomy of an ECM Solution," printout from web address: http://www.aiim.org/infonomics/anatomy-of-an-ecm-solution.aspx, Jul./Aug. 2009, 2 pages.

Gale A. McCarty, "Clinical Trial Protocol Development and Multi-Center Site Management of a Medical Device Clinical Trial Using EMC Documentum eROO™ as a Virtual Workspace," Abstract of paper presented at "Clinical Trials and Clinical Research Expo 2005." Washington, DC, Oct. 24, 2005, 2 pages.

"Collaboration Platform unifies Bio-Pharm data, processes," Feb. 12, 2008, printout from web address: http://news.thomasnet.com/fullstory/539739, Tourtellotte Solutions Fusion DMC, 4 pages.

Ashish Kumar, "Digital Collaboration," Avanade Point of View, printout from web address: <http://www.collaboratesimply.com/images/Avanade_DigitalCollaboration.pdf>, printout date: Nov. 2009, original posting date: unknown, 15 pages.

"Effective Due Diligence," printout from web address: http://pharmalicensing.com/public/articles/view/995877551_3b5be2af61e34, printout date: Nov. 16, 2009, original posting date: unknown, 14 pages.

"EMC Solutions for Life Sciences," printout from web address: http://canada.emc.com/collateral/industry-overview/h2131-life-sciences-brochure.pdf, Copyright © 2006 EMC Corporation, 12 pages.

Francois Gossieaux, "Enabling Collaboration in the Pharmaceutical Industry," BioPharm, Jun. 2002, pp. 105-106, 2 pages.

FirstPoint™ Enterprise Content Management product brochure. Copyright © 2008 Computer Sciences Corporation, 12 pages.

"Protecting Sensitive Information in Life Sciences Organizations: Top Three Misconceptions that put Companies At Risk," Whitepaper from Brainloop (www.brainloop.com <http://www.brainloop.com>), printout date: Nov. 2009, original posting date: unknown, 10 pages.

"Electronic Clinical Trial System Development with SharePoint," Copyright 2008—Shinetech Software Inc., http://www.shinetechchina.com/softwave/case_study/Web_parts.htm, original posting date: unknown, 3 pages.

\* cited by examiner

Figure 2

| | | | | | | |
|---|---|---|---|---|---|---|
| | TruPoints Designer | | | | | |

TruPoints Designer                                           -5132 (Change Project)

User | Projects | Companies | Login History | Activity Monitor | Activity Summary | Content | Categories |
Category Default | Sub-Categories | Documents View | Documents Search | Static Charts | Log Out

| add user | Users | Company | Project | Protocol | Policy Name | Status |
|---|---|---|---|---|---|---|
| View/Edit | | Company A | | 09-001 | V7 TruPoints – Default | Active |
| View/Edit | | Company N | | 09-001 | V7 TruPoints – Default | Active |
| View/Edit | | Company M | | 09-001 | V7 TruPoints – Default | Active |
| View/Edit | | Numoda | | 09-001 | V7 TruPoints – Admin | Active |
| View/Edit | | Numoda | | 09-001 | V7 TruPoints – Admin | Active |
| View/Edit | | Numoda | | 09-001 | V7 TruPoints – Default | Expired |
| View/Edit | | Company S | | 09-001 | V7 TruPoints – Default | Active |
| View/Edit | | Company N | | 09-001 | V7 TruPoints – Default | Active |
| View/Edit | | Company M | | 09-001 | V7 TruPoints – Default | Active |
| View/Edit | | Company A | | 09-001 | V7 TruPoints – Default | Active |
| View/Edit | | Company T | | 09-001 | V7 TruPoints – Default | Locked |
| View/Edit | | Company A | | 09-001 | V7 TruPoints – Default | Active |
| View/Edit | | Company A | | 09-001 | V7 TruPoints – Default | Active |
| View/Edit | | Company S | | 09-001 | V7 TruPoints – Default | Active |
| View/Edit | | Company A | | 09-001 | V7 TruPoints – Default | Active |

Figure 3 (Prior Art)

| Client Name | |

Client Logo

| | V6.5 User Management User List \| User List Report\|Print User ID Sheet\| Policy Report |
|---|---|
| Startup and Regulatory Administration | |
| Clinical Project Accounting | |

Screening and Enrollment Tools — User List   Active Only \| Inactive Only

| | Users | Group Policy | Role | Add user |
|---|---|---|---|---|
| Document Management System | | V6.5- RePortal IVRAdmin | IVRAdmin | View/Edit |
| Project Management Administration Tools | | V6.5- RePortal IVRAdmin | IVRAdmin | View/Edit |
| Early Safety Signal Detection System | | V6.5- RePortal IVRAdmin | IVRAdmin | View/Edit |
| Monitoring System | | V6.5- RePortal Admin | Admin | View/Edit |
| Data Management and Integrations | | V6.5- RePortal PM | PM | View/Edit |
| | | V6.5- RePortal PM | PM | View/Edit |
| Real-Time Reporting Tools | | | | |
| Supplies Management Systems | | V6.5- RePortal Admin | Admin | View/Edit |
| | | V6.5- RePortal MON | Mon | View/Edit |
| IVR/IWR Administration | | V6.5- RePortal IVRAdmin | IVRAdmin | View/Edit |
| Clinical Site Direct Access | | | | |
| TruPoints | | V6.5- RePortal PM Level 2 | PM | View/Edit |
| Portal Main Page | | V6.5- RePortal PM | PM | View/Edit |
| Log Off | | V6.5- RePortal PM | PM | View/Edit |
| | | V6.5- RePortal IVRAdmin | IVRAdmin | View/Edit |
| | | V6.5- RePortal PM | PM | View/Edit |
| | | V6.5- RePortal PM | PM | View/Edit |
| | | V6.5- RePortal Admin | Admin | View/Edit |
| | | V6.5- RePortal Admin | Admin | View/Edit |
| | | V6.5- RePortal Admin | PM | View/Edit |
| | | V6.5- RePortal IVRAdmin | IVRAdmin | View/Edit |
| | | V6.5- RePortal Admin | Admin | View/Edit |
| | | V6.5- RePortal PM | PM | View/Edit |
| | | V6.5- RePortal Admin | Admin | View/Edit |

Figure 5

| Column Name | Display Type | Data Field | Comments |
|---|---|---|---|
| Subject | Label | patientID | |
| CRF Status | Label | status | |
| Adverse Event | Label | AE_Description | |
| Is SAE | Label | AE_serious | |
| Start Date | Label | StartDate | |
| End Date | Label | endDate | |
| Severity | Label | AE_Severity | |
| Relation | Label | AE_Relation | |
| Outcome | Label | AE_Outcome | |
| Action Taken | Label | AE_Action2 | |
| Action Taken with StudyMed | Label | AE_Action | |

Figure 6 (Prior Art)

| Data Schema | | |
|---|---|---|
| | Adverse Events | |

| tblAE | | |
|---|---|---|
| PK | PatientID | varchar(6) |
| PK | AE_ID | int |
| PK | AE_Number | int |
| | Status | varchar(2) |
| | LockFlag | varchar(2) |
| | AE_Description | varchar(1000) |
| | StartDate | varchar(25) |
| | StartTime | varchar(20) |
| | endDate | varchar(25) |
| | endTime | varchar(20) |
| | AE_Serious | varchar(2) |
| FK1 | AE_Severity | varchar(20) |
| | AE_Action2 | varchar(20) |
| | AE_Relation | varchar(20) |
| | AE_CTC | varchar(20) |
| | AE_Conmed | varchar(20) |
| | AE_Outcome | varchar(20) |
| | AE_comment | varchar(500) |
| | AE_PriorDose | varchar(20) |
| | SAEData | varchar(5000) |

| AE_Definitions | |
|---|---|
| Type | varchar(40) |
| value | varchar(50) |
| description | varchar(100) |

| AddtlData_PatientIDs | | |
|---|---|---|
| PK | PatientIDsIndex | int identity |
| | MobileID | int |
| | PatientNumber | int |
| | PatientID | varchar(50) |
| | PatientInitials | varchar(50) |
| | UserID | varchar(50) |
| | LastUpdate | datetime |
| | UpdatedBy | varchar(50) |

| Admin_MobileIDs | |
|---|---|
| | |
| Admin_MobileIDsIndex | int identity |
| SiteID | int |
| MobileID | int |
| SerialNumber | varchar(255) |
| AssetNumber | varchar(255) |
| DescriptionBlock | varchar(500) |
| CommentsBlock | varchar(500) |
| eCRF_Protocol | int |
| eCRF_Language | int |
| eCRF_Localization | int |
| LastUpdate | datetime |
| UpdatedBy | int |

| View_PatientStatus | |
|---|---|
| PatientID | varchar(6) |
| Status | varchar(10) |
| StatusDescription | varchar(50) |
| ActionDate | datetime |

Figure 8 (Prior Art)

| Client Name | |
|---|---|

Client Logo

| | |
|---|---|
| Startup and Regulatory Administration | |
| Planning Procurement and Contracting | |
| Clinical Project Accounting | |
| Screening and Enrollment Tools | |
| Document Management System | |
| Project Management Administration Tools | |
| Early Safety Signal Detection System | |
| Monitoring System | |
| Data Management and Integrations | |
| Real-Time Reporting Tools | |
| Supplies Management Systems | |
| IVR/IWR Administration | |
| Clinical Site Direct Access | |
| TruPoints | |
| Portal Main Page | |
| Log Off | |

AE Report
Client Protocol Number

| | Total | |
|---|---|---|
| AE #: | 181 | |
| SAE #: | 5 | |
| Discontinued #: | 2 | |

Selection Criteria

| Country | All |
|---|---|
| Site | All |
| Intensity | All |
| Action taken regarding study medication | All |
| Action taken regarding Adverse Events | All |
| Relationship | All |
| Event Outcome | All |
| Frequency | All |
| Is adverse event serious? | All |
| Total selected AE # | 181 |

| SubjectID: 101007  Track#: 1  AE Type:  AE Status: Complete | |
|---|---|
| Adverse Event: | Hypertension |
| Date Reported: | 04 Jan 2010 |
| Start Date: | 04 Jan 2010 10:30:00 |
| End Date: | 14 Jan 2010 12:56:00 |
| Intensity: | Moderate |
| Action taken regarding study medication: | None |
| Action taken regarding Adverse Events | Patient withdrawn (ET) from study due to this AE |
| Relationship: | Not Related |
| Event Outcome: | Adverse Event resolved or stabilized |
| Frequency: | Intermittent |
| Is adverse event serious?: | Not Serious |
| Comments: | Patient withdrawn screen failure |

Figure 9 (Prior Art)

| Column Name | Display Type | Data Field | Comments |
|---|---|---|---|
| SubjectID | HyperLink | patientID | Patient ID |
| Track# | Label | AE_Number | AE Number |
| AE Type | Label | AEType | Values can be AE/SAE |
| Status | Label | status | AE Status |
| Adverse Event | Label | AE_Description | AE Description |
| Date Reported | Label | AE_CTC | |
| Start Date | Label | AE_StartDate | |
| End Date | Label | AE_StopDate | |
| Intensity | Label | AE_Severity | |
| Action taken regarding study medication : | Label | AE_Action | |
| Action Taken regarding Adverse Event | Label | AE_Action2 | |
| Relationship | Label | AE_Relation | |
| Event Outcome | Label | AE_Outcome | |
| Frequency | Label | AE_EventRecurrent | |
| Is adverse event serious? | Label | AE_serious | |
| Comments | Label | AE_comment | |

Figure 10 (Prior Art)

https://www.mynumoda.com/eCRF_Report...

Patient: 101003, JRD

Unscheduled

| eCRF Name | Screening | Cold Room | | | | | Follow-Up |
|---|---|---|---|---|---|---|---|
| | Day -2 to -45 | Visit 2 Day 0 | Visit 3 Day 2 | Visit 4 Day 5 | Visit 5 Day 7 | Visit 6 Day 10 | Visit 7 Day 17 |
| | 16 Nov 2009 | 30 Nov 2009 | 03 Dec 2009 | 08 Dec 2009 | 10 Dec 2009 | 14 Dec 2009 | 18 Dec 2009 |
| Informed Consent/Demographics | L | -- | -- | -- | -- | -- | -- |
| Inclusion/Exclusion | L | -- | -- | -- | -- | -- | -- |
| Medical History | L | -- | -- | -- | -- | -- | -- |
| Previous History | L | -- | -- | -- | -- | -- | -- |
| Physical Examination | L | -- | -- | -- | -- | L | -- |
| Current Disease | L | -- | -- | -- | -- | -- | -- |
| Disease Questionnaire | L | -- | -- | -- | -- | -- | -- |
| Vital Signs | L | -- | -- | -- | -- | L | -- |
| Lab Collections | L | -- | -- | -- | -- | L | -- |
| General Assessments | -- | L | L | L | L | L | L |
| Disease Assessments | -- | L | L | L | L | L | L |
| Pre-Exposure Period | -- | L | L | L | L | L | -- |
| Cold Room Exposure | -- | L | L | L | L | L | -- |
| Disease Phenom During Exposure | -- | L | L | L | L | L | -- |
| Warm Room Exposure | -- | L | L | L | L | L | -- |
| Disease Condition Score | -- | L | L | L | L | L | -- |
| End of Day Symptoms | -- | L | L | L | L | L | -- |
| Physician/Cold Room Observer Assessment | -- | L | L | L | L | L | -- |
| Randomization/Dispense Study Medication | -- | L | L | L | L | -- | -- |
| Main Disease Symptom | -- | L | L | L | L | L | -- |
| Collect Study Medication | -- | -- | L | L | L | L | -- |
| Patient Status | L | L | L | L | L | L | L |
| Adverse Events | | | | L | | | |
| Prior and Concomitant Medications | | | | L | | | |

Query Preview  (50 Queries: 0 Posted, 0 Pending, 50 Completed)    LABs

[C] Complete   [P] Pending   [I] Incomplete   [M] Missed
[L] Complete and Locked   [--] Not Required Figure 11 (Prior Art)

> https://www.mynumoda.com/eCRF_Report...
>
> CRF:Informed Consent/Demographics
> Subject:101003  Initial:JRD  Birthday: 28 JAN 1984
> Visit: DAY -2 TO -45
> Visit Date: 11/16/2009
> Completed: Jan 7 2010 2:48PM
>
> ---
>
> Date of Informed Consent:
>
> Date:
>
> | Day | Month | Year |
> |-----|-------|------|
> | 16  | NOV   | 2009 |
>
> [Generate Query]   [Query History]   [Audit History]
>
> ---
>
> Please enter the patient's demographic information:
>
> Date of Birth:        28 JAN 1984
>
> Gender:        ○ Female    ○ Male
>
> Ethnicity:     Non-Hispanic or Non-Latino
>
> [Generate Query]   [Query History]   [Audit History]
>
> ---
>
> Race
>
> ☐ American Indian or Alaskan Native
> ☐ Asian
> ☐ Black or African American
> ☐ Native Hawaiian or other Pacific Islander
> ☑ White

Figure 12 (Prior Art)

| Client Logo | Client Name | | | | | | | | | | |
|---|---|---|---|---|---|---|---|---|---|---|---|
| Startup and Regulatory Administration | | | | | | | | | | | |
| Planning Procurement and Contracting | Please select a site | All Sites | | Run Report | | | | | | | |
| Clinical Project Accounting | | | | | | | | | | | |
| Screening and Enrollment Tools | Site Supplies Summary Report for site: All Sites<br>Client Protocol # | | | | | | | | | | |
| Document Management System | Site ID: 101 Dr. X, MD | | | | | | | | | | |
| Project Management Administration Tools | Patient ID | Status | DOB | Gender | Peak Score/MRS at V2 | Peak Score/MRS V3 | Peak Score/MRS at V4 | Peak Score/ MRS at V5 | Peak Score/ MRS at V6 | V2 Qualifier | Randomi-zation |
| Early Safety Signal Detection System | 10001 | V2 Failure | 02 Nov 1938 | M | IWR: 7-Numbness<br>CRF: 7-Numbness | IWR: Numbness<br>CRF: 47-Pain | IWR: 63-Pain<br>CRF: 63-Pain | | | | |
| Monitoring System | | | | | | | | | | | |
| Data Management and Integrations | 10002 | Randomization Failure | 26 Feb 1960 | F | IWR: 41-Pain<br>CRF: 41-Pain | IWR: 71-Pain<br>CRF: 71-Pain | IWR: 33-Pain<br>CRF: 33-Pain | | | 671 (15 Dec 2009) | |
| Real-Time Reporting Tools | | | | | | | | | | | |
| Supplies Management Systems | 10003 | Completed | 28 Jan 1984 | M | IWR: 60-Pain<br>CRF: 60-Pain | IWR: 47-Pain<br>CRF: 47-Pain | IWR: 63-Pain<br>CRF: 63-Pain | CRF: 75-Pain | CRF: 40-Pain | 609 (30 Nov 2009) | |
| IVR/IWR Administration | | | | | | | | | | | |
| Clinical Site Direct Access | 10004 | Randomization Failure | 26 Nov 1952 | F | IWR: 67-Pain<br>CRF: 67-Pain | IWR: 66-Pain<br>CRF: 66-Pain | IWR: 33-Pain<br>CRF: 33-Pain | | | 670 (07 Dec 2009) | 4001 (08 Dec 2009) |
| TruPoints | | | | | | | | | | | |
| Portal Main Page | | | | | | | | | | | |
| Log Off | | | | | | | | | | | |

Figure 14

| Column Name | Display Type | Data Field | Comments |
|---|---|---|---|
| Patient ID | Label | PatientID | |
| Status | Label | DSName | |
| DOB | Label | DOB | |
| Gender | Label | Gender | |
| Peak Score/MRS at V2 | Label | IWR_v2PeakScore<br>IWR_MRS<br>v2PeakScore<br>v2MRS | |
| Peak Score/MRS at V3 | Label | IWR_v3PeakScore<br>IWR_MRS<br>v3PeakScore<br>v3MRS | |
| Peak Score/MRS at V4 | Label | IWR_v4PeakScore<br>IWR_MRS<br>v4PeakScore<br>v4MRS | |
| Peak Score/MRS at V5 | Label | v5PeakScore<br>v5MRS | |
| Peak Score/MRS at V6 | Label | v6PeakScore<br>v6MRS | |

Figure 18 (Prior Art)

| Column Name | Display Type | Data Field | Comments |
|---|---|---|---|
| Patient ID | Hyperlink | PatientID | |
| Status | Label | statusDescription | |
| DOB | Label | DOB | |
| Gender | Label | Gender | |
| Peak Score/MRS at V2 | Label | IWR_v2PeakScore<br>IWR_MRS<br>v2PeakScore<br>v2MRS | |
| Peak Score/MRS at V3 | Label | IWR_v3PeakScore<br>IWR_MRS<br>v3PeakScore<br>v3MRS | |
| Peak Score/MRS at V4 | Label | IWR_v4PeakScore<br>IWR_MRS<br>v4PeakScore<br>v4MRS | |
| Peak Score/MRS at V5 | Label | v5PeakScore<br>v5MRS | |
| Peak Score/MRS at V6 | Label | v6PeakScore<br>v6MRS | |
| V2 Qualifier | Hyperlink | RunInKit<br>RunInDate<br>patientID | |
| Randomization | Hyperlink | ActiveKit<br>ActiveDate<br>patientID | |

Figure 19 (Prior Art)

| Data Schema |
|---|
| Site Supplies Summary |

| View_PatientPeakScore | |
|---|---|
| patientID | varchar(100) |
| initial | varchar(50) |
| DOB | varchar(8000) |
| Gender | varchar(8000) |
| status | varchar(10) |
| statusDescription | varchar(50) |
| v1PeakScore | varchar(8000) |
| v1MRS | varchar(30) |
| v2PeakScore | varchar(8000) |
| v2MRS | varchar(30) |
| v3PeakScore | varchar(8000) |
| v3MRS | varchar(30) |
| v4PeakScore | varchar(8000) |
| v4MRS | varchar(30) |
| v5PeakScore | varchar(8000) |
| v5MRS | varchar(30) |
| v6PeakScore | varchar(8000) |
| v6MRS | varchar(30) |

| View_PatientRaynaudSymptoms | |
|---|---|
| UserID | varchar(100) |
| ansData | varchar(8000) |
| Visit | int |
| fldID | int |
| MRS | text |

| view_RunInPatient | |
|---|---|
| patientID | varchar(6) |
| Status | varchar(20) |
| DOB | varchar(50) |
| Gender | varchar(50) |
| MRS | varchar(50) |
| MRSSV2 | varchar(50) |
| KitNumber | varchar(20) |
| AssignDate | datetime |
| LastUpdate | datetime |

| view_RandomPatient | |
|---|---|
| patientID | varchar(6) |
| Status | varchar(20) |
| DOB | varchar(50) |
| Gender | varchar(50) |
| MRS | varchar(50) |
| MRSSV2 | varchar(50) |
| MRSSV3 | varchar(50) |
| MRSSV4 | varchar(50) |
| Stratum | Int |
| KitNumber | varchar(20) |
| AssignDate | datetime |

| view_PatientList | |
|---|---|
| patientID | varchar(100) |
| initial | varchar(50) |
| DOB | varchar(8000) |
| Gender | varchar(8000) |

| View_PatientStatus | |
|---|---|
| PatientID | varchar(6) |
| Status | varchar(10) |
| StatusDescription | varchar(50) |
| ActionDate | datetime |

| view_PatientRecord | |
|---|---|
| patientID | varchar(100) |
| surveyID | Int |
| visit | int |
| fldID | int |
| value | varchar(8000) |
| complete | datetime |

Figure 20 (Prior Art)

https://www.mynumoda.com/IVRS_Report....

Client Protocol # Cold Room Challenge Confirmation:
*******************************

Cold Room Challenge Confirmation

This is an automated message for the client.
Please contact the IWR Help desk at 888-475-3640 if you have any questions.

Site Number: 101
PI Name: 
Site Name: UM
Address: Clinical Research Center Acute Care Building, 3rd Floor, The IWR system has processed the following transaction:

Patient: 101002
Date of Birth: 26 Feb 1960
Gender: F
Most bothersome symptom selected: Pain
Highest score for MRS at V2: 48

Assigned Kit Number: 671
Assigned Time: Dec 15 2009 5:33PM(EST)
 Component for Visit 3 take-home: 67101
 Component for Visit 3 in-clinic: 67102
 Component for Visit 4 take-home: 67103
 Component for Visit 4 in-clinic: 67104

Figure 21 (Prior Art)

```
┌─────────────────────────────────────────────────────────────────────┐
│    ┌──────────────────────────────────────────┐ ┌─────────────┐     │
│    │   https://www.mynumoda.com/IVRS_Report...│ │             │     │
├────┴──────────────────────────────────────────┴─┴─────────────┴─────┤
│ Client Protocol # Randomization Confirmation:                        │
│ ***********************************************                     │
│ Randomization Confirmation                                           │
│                                                                      │
│ This is an automated message for the client.                         │
│ Please contact the IWR Help desk at 888-475-3640 if you have any questions. │
│                                                                      │
│ Site Number: 101                                                     │
│ PI Name: ▓▓▓▓ ▓▓▓                                                    │
│ Site Name: UM▓▓▓                                                     │
│ Address: ▓▓▓▓▓▓▓▓▓▓▓▓▓▓▓▓▓▓▓▓▓▓ Clinical Research Center Acute Care Building, 3rd Floor, P.O. │
│ Box ▓▓ ▓▓ ▓▓▓▓▓▓ ▓▓▓▓▓, ▓▓▓▓▓▓▓▓▓, ▓▓ ▓▓▓▓▓-▓▓ 9                     │
│                                                                      │
│ The IWR system has processed the following transaction:              │
│                                                                      │
│ Patient: 101003                                                      │
│ Date of Birth: 28 Jan 1984                                           │
│ Gender: M                                                            │
│ Highest score for MRS at V2: 60                                      │
│ Peak MRS score at V3: 47                                             │
│ Peak MRS score at V4: 63                                             │
│                                                                      │
│ Assigned Kit Number: 4001                                            │
│ Assigned Time: Dec 8 2009 5:33PM(EST)                                │
│    Component for Visit 5 take-home: 400105                           │
│    Component for Visit 5 in-clinic: 400106                           │
│    Component for Visit 6 take-home: 400107                           │
│    Component for Visit 6 in-clinic: 400108                           │
│                                                                      │
└─────────────────────────────────────────────────────────────────────┘
```

Figure 23

| | TruPoints Designer | |

TruPoints Designer          ▓▓▓▓-5132 (Change Project)

User| Projects| Companies| Login History| Activity Monitor| Activity Summary| Content| Categories|
Category Default | Sub-Categories| Documents View| Documents Search | Static Charts | Log Out

| add user | Users | Company | Project | Protocol | Policy Name | Status |
|---|---|---|---|---|---|---|
| View/Edit | ▓▓▓ | Partner ABC | ▓▓▓ | ▓▓▓ 09-001 | V7 TruPoints – Default | Active |
| View/Edit | ▓▓▓ | Investor CDE | ▓▓▓ | ▓▓▓ 09-001 | V7 TruPoints – Default | Active |
| View/Edit | ▓▓▓ | XYZ Corp. | ▓▓▓ | ▓▓▓ 09-001 | V7 TruPoints – Default | Active |
| View/Edit | ▓▓▓ | Numoda | ▓▓▓ | ▓▓▓ 09-001 | V7 TruPoints – Admin | Active |
| View/Edit | ▓▓▓ | Numoda | ▓▓▓ | ▓▓▓ 09-001 | V7 TruPoints – Admin | Active |
| View/Edit | ▓▓▓ | Numoda | ▓▓▓ | ▓▓▓ 09-001 | V7 TruPoints – Default | Expired |
| View/Edit | ▓▓▓ | Investor FGH | ▓▓▓ | ▓▓▓ 09-001 | V7 TruPoints – Default | Active |
| View/Edit | ▓▓▓ | ▓▓▓ | ▓▓▓ | ▓▓▓ 09-001 | V7 TruPoints – Default | Active |

Figure 26

| | Category | Status | add category |
|---|---|---|---|
| ▲▼ | Default | Inactive | View/Edit |
| ▲▼ | Insurance | Active | View/Edit |
| ▲▼ | Intellectual Property | Active | View/Edit |
| ▲▼ | Marketing | Active | View/Edit |
| ▲▼ | Material Agreements | Active | View/Edit |
| ▲▼ | Regulatory | Active | View/Edit |

TruPoints Designer

TruPoints Designer                                       -5132 (Change Project)

User | Projects | Companies | Login History | Activity Monitor | Activity Summary | Content | Categories | Category Default | Sub-Categories | Documents View | Documents Search | Static Charts | Log Out Project:
Category: Business Information

Figure 27

Business Information | Scientific | CMC | Current Studies

⊗ Insurance           ⊗ Intellectual Property   ⊗ Marketing
⊗ Material Agreements ⊗ Regulatory

Figure 28

| | Category | Status | add category |
|---|---|---|---|
| | TruPoints Designer | | |

TruPoints Designer  ▬▬▬ -5132 (Change Project)

User| Projects| Companies| Login History |Activity Monitor| Activity Summary| Content| Categories| Category Default | Sub-Categories| Documents View| Documents Search | Static Charts | Log Out Project: ▬▬▬
Category: Scientific ⌄

| | Category | Status | add category |
|---|---|---|---|
| ⇕ | Abstracts and Publication | Active | View/Edit |
| ⇕ | Investigator Brochure | Active | View/Edit |
| ⇕ | NDA | Active | View/Edit |
| ⇕ | PI Interviews | Active | View/Edit |
| ⇕ | PK Studies | Active | View/Edit |
| ⇕ | Phase II Studies | Active | View/Edit |
| ⇕ | Phase III Studies | Active | View/Edit |
| ⇕ | Post NDA Studies | Active | View/Edit |
| ⇕ | Open Label Studies | Active | View/Edit |
| ⇕ | Protocol 03-001 | Inactive | View/Edit |
| ⇕ | Protocol 05-001 | Inactive | View/Edit |
| ⇕ | Protocol 06-005 | Inactive | View/Edit |
| ⇕ | Protocol 07-003 | Inactive | View/Edit |
| ⇕ | Protocol 07-005 | Inactive | View/Edit |
| ⇕ | Protocol 08-001 | Inactive | View/Edit |
| ⇕ | Protocol 09-002 | Inactive | View/Edit |
| ⇕ | Preclinical | Active | View/Edit |

Figure 30

| | | | | | | | | | | | Milestone Groups | | | | | | |
|---|---|---|---|---|---|---|---|---|---|---|---|---|---|---|---|---|---|
| ID | Principal Investigator | Country | Site ID | Status | QUAL | SITE DOCS | IRB/EC | REG DOCS | CON-TRACT | BUDGE | MATS | IP | Initiate |
| T1 | | United States | 101 | Complete | 2/2 | 7/7 | 12/12 | 6/6 | 4/4 | 3/3 | 17/17 | 7/7 | 5/5 |
| T2 | | United States | 102 | Complete | 2/2 | 10/10 | 12/12 | 6/6 | 4/4 | 3/3 | 17/17 | 7/7 | 5/5 |
| T3 | | United States | 103 | Complete | 2/2 | 10/10 | 12/12 | 6/6 | 4/4 | 3/3 | 17/17 | 7/7 | 5/5 |
| T4 | | United States | 111 | Complete | 2/2 | 10/10 | 12/12 | 6/6 | 4/4 | 3/3 | 17/17 | 7/7 | 5/5 |
| T5 | | United States | 106 | Complete | 2/2 | 7/7 | 12/12 | 6/6 | 4/4 | 3/3 | 17/17 | 7/7 | 5/5 |
| T6 | | United States | 107 | Complete | 2/2 | 10/10 | 12/12 | 6/6 | 4/4 | 3/3 | 17/17 | 7/7 | 5/5 |
| T7 | | United States | 108 | Complete | 2/2 | 10/10 | 12/12 | 6/6 | 4/4 | 3/3 | 17/17 | 7/7 | 5/5 |
| T11 | | United States | 104 | Complete | 2/2 | 7/7 | 12/12 | 6/6 | 4/4 | 3/3 | 17/17 | 7/7 | 5/5 |
| T12 | | United States | 110 | Complete | 2/2 | 10/10 | 12/12 | 6/6 | 4/4 | 3/3 | 17/17 | 7/7 | 5/5 |
| T13 | | United States | 112 | Complete | 2/2 | 10/10 | 12/12 | 6/6 | 4/4 | 3/3 | 16/16 | 4/4 | 5/5 |
| T14 | | United States | 113 | Complete | 2/2 | 7/7 | 6/6 | 6/6 | 4/4 | 3/3 | 3/3 | 3/3 | 5/5 |

Current Studies – Site Tracker
Site Tracker

| | Complete | Closed | Pending | On Hold | Target | % Target | Milestones | % Milestones |
|---|---|---|---|---|---|---|---|---|
| United States 4/4 | 11 | 0 | 0 | 0 | 11 | 100.00% | 707/707 | 100.00% |
| Total Sites | 11 | 0 | 0 | 0 | 11 | 100.00% | 707/707 | 100.00% |

Tabs: Business Information | Scientific | CMC | Current Studies

TruPoints™ — powered by Numoda Technologies, Inc — Logout

Figure 31

| | TruPoints Designer | | |

TruPoints Designer  -5132 (Change Project)

User | Projects | Companies | Login History | Activity Monitor | Activity Summary | Content | Categories | Category Default | Sub-Categories | Documents View | Documents Search | Static Charts | Log Out Project: 
Category: Scientific

| | Category | Status | add category |
|---|---|---|---|
| | Abstracts and Publication | Active | View/Edit |
| | Investigator Brochure | Active | View/Edit |
| | NDA | Active | View/Edit |
| | PI Interviews | Active | View/Edit |
| | PK Studies | Active | View/Edit |
| | Phase II Studies | Active | View/Edit |
| | Phase III Studies | Active | View/Edit |
| | Post NDA Studies | Active | View/Edit |
| | Open Label Studies | Active | View/Edit |
| | Protocol 03-001 | Inactive | View/Edit |
| | Protocol 05-001 | Inactive | View/Edit |
| | Protocol 06-005 | Inactive | View/Edit |
| | Protocol 07-003 | Inactive | View/Edit |
| | Protocol 07-005 | Inactive | View/Edit |
| | Protocol 08-001 | Inactive | View/Edit |
| | Protocol 09-002 | Inactive | View/Edit |
| | Preclinical | Active | View/Edit |

Sub-category
Abstracts and Publications

Project: 
Category: Scientific
Page URL:

Description

Document list ☑
Active ☑
Last Updated 7/29/2009 01:04:45PM
Last Updated by

Save    Change

Figure 33

Current Studies – Subject Status

Patient Status Key
AS=Active Screened IS=Idle Screened SF=Screen Failure V2Q=V2 Qualified V2F=V2 Failure V3C=V3 Completer R=Randomized
RF=Randomization Failure D=Discontinued C=Completed

Counts Legend
C=Complete L=Locked I/P=InComplete Q=Queries

| Patient ID | Init | Status | Date Randomized/(Screened) | Date Disc'ned | Screening Day -2 to -14 | Cold Room Visit 2 Day 0 | Cold Room Visit 3 Day 2 | Cold Room Visit 4 Day 5 | Cold Room Visit 5 Day 7 | Follow-up Visit 6 Day 10 | C | L | I/P | Q |
|---|---|---|---|---|---|---|---|---|---|---|---|---|---|---|
| 101001 | M-I | V2F | (11/16/2009) | 12/08/2009 | 11/16/2009 | 12/08/2009 | | | | 12/17/2009 | 31 | 31 | 11 | 0 |
| 101002 | HLS | RF | (11/16/2009) | 12/22/2009 | 11/16/2009 | 12/15/2009 | 12/17/2009 | | 12/22/2009 | 12/29/2009 | 57 | 56 | 11 | 1 |
| 101003 | JRD | C | 12/08/2009 | | 11/16/2009 | 11/30/2009 | 12/03/2009 | 12/10/2009 | 12/14/2009 | 12/18/2009 | 81 | 81 | 0 | 0 |
| 101004 | SAG | RF | (11/30/2009) | 12/14/2009 | 11/30/2009 | 12/07/2009 | 12/09/2009 | | 12/14/2009 | 12/22/2009 | 57 | 57 | 11 | 0 |
| 101005 | PMW | V2F | (12/03/2009) | 12/16/2009 | 12/03/2009 | 12/16/2009 | | | 12/16/2009 | 12/22/2009 | 31 | 31 | 11 | 0 |
| 101006 | J-P | V2F | (12/03/2009) | 12/09/2009 | 12/03/2009 | 12/09/2009 | | | 12/09/2009 | 12/09/2009 | 15 | 15 | 27 | 0 |
| 101007 | AMM | SF | (01/04/2010) | | 01/04/2010 | | | | | | 12 | 12 | 36 | 0 |
| 101008 | LKM | C | 01/25/2010 | | 01/14/2010 | 01/19/2009 | 01/22/2010 | 02/01/2010 | 02/01/2010 | 02/05/2010 | 81 | 81 | 0 | 0 |

Figure 34

| Business Information | Scientific | CMC | Current Studies |
|---|---|---|---|
| ⊗ Protocol 09-001<br>⊗ Safety Data Summary | ⊗ Protocol 09-002<br>⊗ Site Tracker | ⊗ Site Info<br>⊗ Subject Status | |

Figure 35

| Business Information | Scientific | CMC | Current Studies |
|---|---|---|---|
| ⊗ Protocol 09-001<br>⊗ Safety Data Summary | ⊗ Protocol 09-002<br>⊗ Site Tracker | ⊗ Site Info | |

Figure 36

| TruPoints™ |

TruPoints
NUMODA
powered by Numoda Technologies, Inc

[ Logout ]

| Client Logo | Business Information | Scientific | CMC | Current Studies |

Current Studies – Protocol 09-001

09-001 protocol with amend 3 04Feb2010 (PDF)
A Study of a Topical Formulation of ▒▒▒▒, ▒▒▒▒, and Matching Vehicle in the Treatment and Prevention for Symptoms Associated with ▒▒▒ Phenomenon – Incorporating Amendments 1, 2, and 3

09-001 protocol with amend 2 final Oct 5 2009 (PDF)
A Study of a Topical Formulation of ▒▒▒▒, ▒▒▒▒, and Matching Vehicle in the Treatment and Prevention for Symptoms Associated with ▒▒▒ Phenomenon – Incorporating Amendments 1 and 2

09-001 Amendment 2 changes list 03Oct2009 final (PDF)
Summary of Protocol 09-001 (As Amdned) Changed 09-001 protocol with amend 1 18Jun2009 (PDF)
Clinical study protocol 09-001 for the study entitled "A Study of Topical Formulation of ▒▒▒▒, ▒▒▒▒, and Matching Vehicle in the Treatment and Prevention of Symptoms Assoiciated with ▒▒▒ Phenomenon."

~~▒▒▒▒~~'s Investigator's Brochure v 15 27Mar2009 (PDF)
Investigators brochure, complete summary, and information on ▒▒▒▒.

Figure 38

TruPoints Designer

User | Projects | Companies | Login History | Activity Monitor | Activity Summary | Content | Categories | Category Default | Sub-Categories |
Documents View | Documents Search | Static Charts | Log Out -5132 (Change Project)

Project:
Category: Current Studies
Sub-category: Protocol 09-001

| Documents | Type | PDF Attached | Status | add document |
|---|---|---|---|---|
| 09-001 protocol with amend 3 04Feb2010 (PDF) A Study of a Topical Formulation of _____, and Matching Vehicle in the Treatment and Prevention for Symptoms Associated with _____ Phenomenon – Incorporating Amendments 1, 2, and 3 | PDF | Yes | Active | View/Edit |
| 09-001 protocol with amend 2 final Oct 5 2009 (PDF) A Study of a Topical Formulation of _____, and Matching Vehicle in the Treatment and Prevention for Symptoms Associated with _____ Phenomenon – Incorporating Amendments 1 and 2 | PDF | Yes | Active | View/Edit |
| 09-001 protocol with amend 2 final Oct 5 2009 (PDF) A Study of a Topical Formulation of _____, and Matching Vehicle in the Treatment and Prevention for Symptoms Associated with _____ – Incorporating Amendments 1 and 2 | PDF | Yes | Active | View/Edit |
| 09-001 Amendment 2 changes list 03Oct2009 final (PDF) Summary of Protocol 09-001 (As Amdned) Changed | PDF | Yes | Active | View/Edit |
| 09-001 protocol with amend 1 18Jun2009 (PDF) Clinical study protocol 09-001 for the study entitled "A Study of Topical Formulation of _____, and Matching Vehicle in the Treatment and Prevention of Symptoms Assoicated with _____ Phenomenon." | PDF | Yes | Active | View/Edit |
| Investigator's Brochure v15 27Mar2009 (PDF) Investigators brochure, complete summary, and information on _____. | PDF | No | Inactive | View/Edit |

Figure 39

| TruPoints Designer |

TruPoints Designer          ▓▓▓▓-5132 (Change Project)

User | Projects | Companies | Login History | Activity Monitor | Activity Summary | Content | Categories | Category Default | Sub-Categories | Documents View | Documents Search | Static Charts | Log Out Document Name
09-001 protocol with amend 3 04Feb2010

Description
A study of a Topical Formulation of ▓▓▓▓▓▓, ▓▓▓▓ ▓▓▓ ▓▓▓, and Matching Vehicl in the Treatment and Prevention of Symptoms Associated with ▓▓▓▓▓▓ Phenomenon – Incorporating Amendments 1, 2, and 3

Document Type:    PDF

Location:
D:\TruPointsSecureDocs\▓▓▓▓▓\09-001 protocol with amend 3 04Feb2010 clean.pdf
Delete PDF Sub-Category:    Current Study Protocol 09-001

Active:    ✓

Watermark:    ✓

Last Update:    03/16/2010 2:45:40 PM

Last Update by:    ▓▓▓▓▓

Save    Cancel

Figure 40

| TruPoints™ | |

TruPoints

NUMODA
powered by Numoda Technologies, Inc

[Logout]

Client Logo | Business Information | Scientific | CMC | Current Studies

Current Studies – Protocol 09-001

09-001 protocol with amend 2 final Oct 5 2009 (PDF)
A Study of a Topical Formulation of ▓▓▓▓▓, and Matching Vehicle in the Treatment and Prevention for Symptoms Associated with ▓▓▓ Phenomenon – Incorporating Amendments 1 and 2

09-001 Amendment 2 changes list 03Oct2009 final (PDF)
Summary of Protocol 09-001 (As Amdned) Changed 09-001 protocol with amend 1 18Jun2009 (PDF)
Clinical study protocol 09-001 for the study entitled "A Study of Topical Formulation of ▓▓▓▓▓, and Matching Vehicle in the Treatment and Prevention of Symptoms Assoiciated with ▓▓▓ Phenomenon."

▓▓▓▓ Investigator's Brochure v15 27Mar2009 (PDF)
Investigators brochure, complete summary, and information on ▓▓▓▓.

Figure 61

| Client Logo | Business Information | Scientific | CMC | Current Studies |
|---|---|---|---|---|

| Current Studies – Safety Data Summary ||||||||||| 
|---|---|---|---|---|---|---|---|---|---|---|
| Subject | CRF Status | Adverse Event | Is SAE | Start Date | End Date | Severity | Relation | Outcome | Action Taken | Action Taken with Study Med |
| 100001 | C | Headache | Not Serious | 01 JAN 2010 | 02 JAN 2010 | Mild | Possibly Related | Adverse Event resolved or stabilized | Adverse Event resolved or stabilized | None |
| 100002 | I | Nausea | Serious (report SAE to sponsor) | 15 JAN 2010 | Continuing | Moderate | Probably Related | AE is ongoing at the end of the study | Concomitant Medication Started to treat this AE | Test agent dose modified |

Figure 62

| Client Logo | Business Information | Scientific | CMC | Current Studies |
|---|---|---|---|---|

| Current Studies – Site Info |||
|---|---|---|
| SITE INFO | Site Staff | Address |
| Site ID: 101<br>University of America<br>PI: Ben Casey | John Doe<br>Jane Smith<br>.<br>.<br>.<br>James Johnson | Site Address:<br>John Doe<br>University of America<br>Main Campus, Building 123, Room 99<br>456 Main Street, Bigtown PA 12345 |
| Site ID: 102<br>Universidad de America del Sur<br>PI: Juan Castille | Juanita Doe<br>Jorge Smith<br>.<br>.<br>.<br>Christina Maldonado | Site Address:<br>Juanita Doe<br>Universidad de America del Sur<br>Campus Central, Science Building<br>456 Calle Grande, Mexico City 12345<br>Mexico |

Figure 63

Client Logo | Business Information | Scientific | CMC | Current Studies

Current Studies – Site Tracker

|  | Complete | Closed | Pending | On Hold | Target | % Target | Milestones | % Milestones |
|---|---|---|---|---|---|---|---|---|
| United States 3/4 | 50 | 0 | 0 | 0 | 50 | 100 | 70/70 | 100 |
| Mexico 1/4 | 10 | 0 | 0 | 0 | 10 | 100 | 30/30 | 100 |
| Total Sites |  |  |  |  |  |  |  |  |

| ID | Principal Investigator | Country | Site ID | Status | QUAL | SITEDOCS | IRB/EC | REGDOCS | CONTRACT | BUDGET | MATS | IP | INITIATE |
|---|---|---|---|---|---|---|---|---|---|---|---|---|---|
| T1 |  | United States | 101 | Complete | 30/30 | 10/10 | 12/12 | 6/6 | 4/4 | 3/3 | 17/17 | 7/7 | 5/5 |
|  |  | Mexico | 102 | Complete | 5/5 | 7/7 | 12/12 | 6/6 | 4/4 | 3/3 | 17/17 | 7/7 | 5/5 |

§ Country Status Not Complete

Figure 64

Client Logo | Business Information | Scientific | CMC | Current Studies

Current Studies – Subject Status

AS=Active Screened  IS=Idle Screened  SF=Screen Failure  V2Q=V2 Qualified
V2F=V2 Failure  V3C=V3 Completer  R=Randomized  RF=Randomization Failure
D=Discontinued  C=Completed

*Patient Status Key*

C = Complete  L + L:ocked  I/P = Incomplete  Q = Queries

| Patient ID | Init | Status | Date Randomized/ (Screened) | Date Disc'ned | Screening Day -2 to -14 | Cold Room Visit 2 Day 0 | Cold Room Visit 3 Day 2 | Cold Room Visit 4 Day 5 | Cold Room Visit 5 Day 7 | Follow-up Visit 6 Day 10 | C | L | I/P | Q |
|---|---|---|---|---|---|---|---|---|---|---|---|---|---|---|
| 101001 | M-I | V2F | (11/16/2009) | 12/08/2009 | 11/16/2009 | 12/08/2009 | | | | 12/17/2009 | 31 | 31 | 11 | 0 |
| 101002 | HLS | RF | (11/16/2009) | 12/22/2009 | 11/16/2009 | 12/15/2009 | 12/17/2009 | | 12/22/2009 | 12/29/2009 | 57 | 56 | 11 | 1 |
| 101003 | JRD | C | 12/08/2009 | | 11/16/2009 | 11/30/2009 | 12/03/2009 | 12/10/2009 | 12/14/2009 | 12/18/2009 | 81 | 81 | 0 | 0 |
| 101004 | SAG | RF | (11/30/2009) | 12/14/2009 | 11/30/2009 | 12/07/2009 | 12/09/2009 | | 12/14/2009 | 12/18/2009 | 57 | 57 | 11 | 0 |
| 101005 | PMW | V2F | (12/03/2009) | 12/16/2009 | 12/03/2009 | 12/16/2009 | | | 12/16/2009 | 12/22/2009 | 31 | 31 | 11 | 0 |
| 101006 | J-P | V2F | (12/03/2009) | 12/09/2009 | 12/03/2009 | 12/09/2009 | | | 12/09/2009 | 12/09/2009 | 15 | 15 | 27 | 0 |
| 101007 | AMM | SF | (01/04/2010) | | 01/04/2010 | | | | | | 12 | 12 | 36 | 0 |
| 101008 | LKM | C | 01/25/2010 | | 01/14/2010 | 01/19/2009 | 01/22/2010 | 02/01/2010 | 02/01/2010 | 02/05/2010 | 81 | 81 | 0 | 0 |

US 7,921,125 B1

VIRTUAL DATA ROOM WITH ACCESS TO CLINICAL TRIAL STATUS REPORTS BASED ON REAL-TIME CLINICAL TRIAL DATA

CROSS-REFERENCE TO RELATED APPLICATIONS

This application claims priority to U.S. Provisional Patent Application No. 61/365,904 filed Jul. 20, 2010.

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

A conventional "virtual data room" (VDR) (also, referred to as a "virtual deal room") is an online repository of information that is used to store and distribute documents that need to be shared and disclosed among different entities. A VDR is often used to facilitate the due diligence process during financial transactions, such as a merger and acquisition transaction, or when an entity is deciding whether to make an investment in a company. The VDR replaces a physical data room that previously housed the repository of information, typically in paper form. In a VDR, the documents are stored in electronic format on a central server and accessed via the Internet. VDRs are assumed to be secure and confidential and a login ID and password is typically required to access the VDR. There are dozens of companies that host VDRs such as Merrill Corporation which provides the Merrill DataSite®.

A clinical data management system or CDMS is used in clinical research to manage the data of a clinical trial. The clinical trial data includes patient data collected at investigator sites in case report forms (CRFs) and patient data received back from patient samples sent to labs. The data that resides in a database associated with a CDMS must be protected in many ways, including protection from access by unauthorized persons.

The life science industry has begun to use VDRs for a variety of purposes other than conventional M&A due diligence. For example, VDRs are used by sponsors to allow potential investors and potential licensees to view documents related to clinical trials. Nonetheless, there is still a need in the art to provide additional functionality in VDRs that are used for these purposes, including the ability to view reports generated on-the-fly from real-time clinical data of an ongoing clinical trial study that resides in a CDMS and to allow the host of the VDR to easily control the availability of such reports to users logged into the VDR. The present invention fulfills such needs.

BRIEF SUMMARY OF THE INVENTION

A virtual data room distributes information associated with an investigational product, such as an investigational compound. The information includes documents associated with the investigational product and reports based on live clinical study data of the investigational product.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIGS. 2, 4, 13, 22-31 and 33-64 are user interface display screens for use in accordance with preferred embodiments of the present invention.

FIGS. 3, 8, 10, 11, 12, 20 and 21 are prior art user interface display screens.

FIGS. 5, 14 and 32 show data schemas and data tables for use in accordance with preferred embodiments of the present invention.

FIGS. 6, 7, 9 and 16-19 show prior art data schemas and data tables.

DETAILED DESCRIPTION OF THE INVENTION

Certain terminology is used herein for convenience only and is not to be taken as a limitation on the present invention.

This patent application includes an Appendix having a file named appendix10001-32U1.txt, created on Sep. 24, 2010, and having a size of 62,769 bytes. The Appendix is incorporated by reference into the present patent application. One preferred embodiment of the present invention is implemented via the source code in the Appendix. The Appendix is subject to the "Copyright Notice and Authorization" stated above.

The present invention is described in the context of features provided in a web-based commercially available virtual data room product/service called TruPoints® marketed by Numoda Capital Innovations LLC, which is an investment and financing affiliate of Numoda® Corporation (Numoda), Philadelphia, Pa. Numoda Capital Innovations LLC hosts TruPoints. However, the scope of the present invention is not limited to this particular implementation of the invention. The present invention is described in the context of a plurality of distributed computers, all of which are linked together by an electronic network, such as a LAN or the Internet. The computers may be any type of computing device that allows a user to interact with a web site via a web browser. For example, the computers may be personal computers (PC) that run a Microsoft Windows® operating system. The computers may also be handheld, wireless devices.

The user interface display screens preferably appear within a browser. However, to simplify the illustrations of the display screens, the browser shells are not shown in the figures.

A. Hardware/Software Elements of TruPoints

Figure 1:
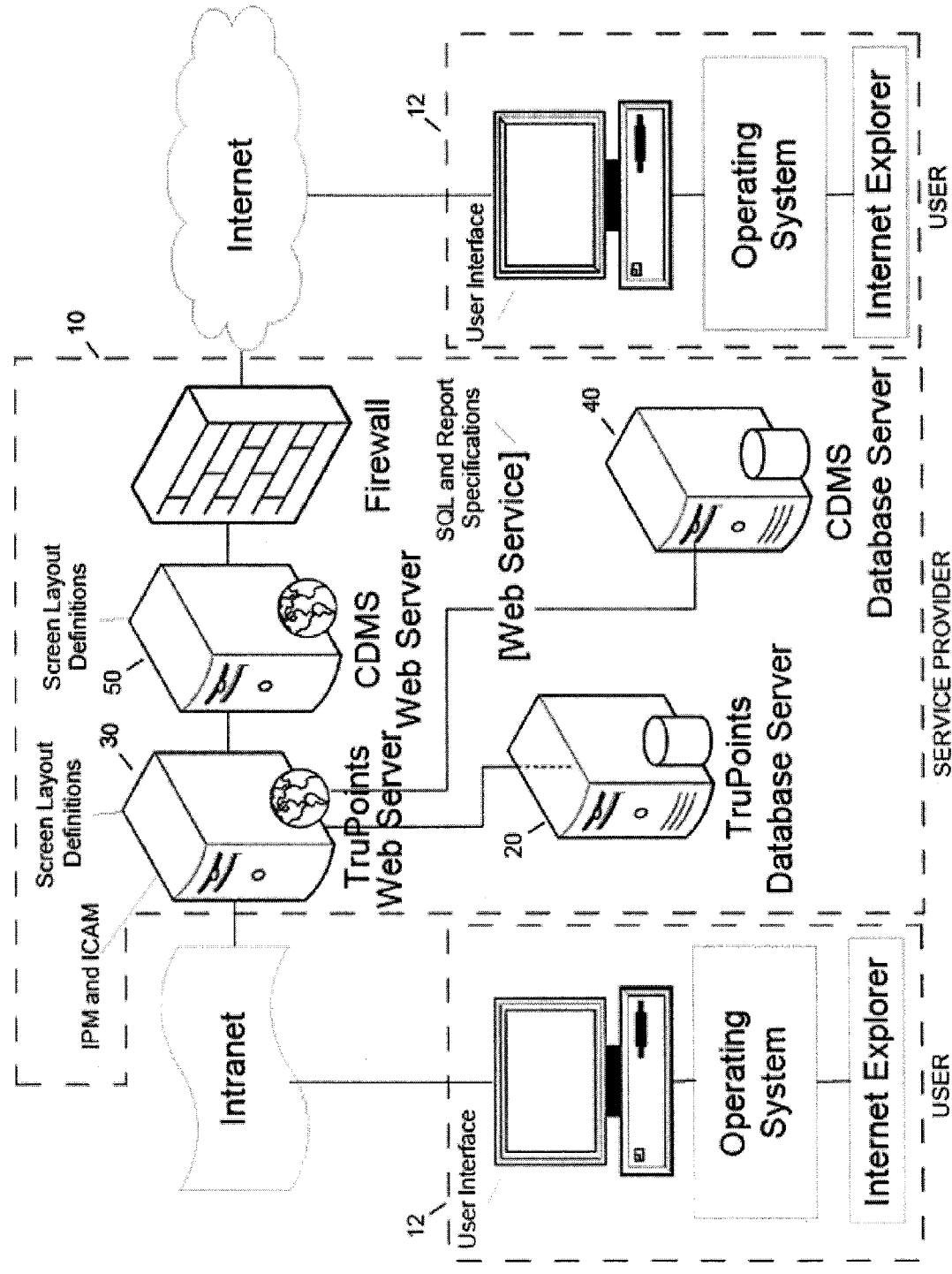
FIG. 1 is a schematic diagram of a hardware configuration in accordance with one preferred embodiment of the present invention.
Figure 4:

FIG. 1 shows one preferred embodiment of the hardware and software elements of the TruPoints (Service Provider) platform 10 (virtual data room) and the user computers 12 that interact with the platform 10. The TruPoints Database Server 20 holds the data related to the navigation, documents and security for the Information Control Administration Module (ICAM) and the Information Presentation Module (IPM) web sites, described in more detail below. The TruPoints Web Server 30 hosts the ICAM and IPM web sites and holds the Screen Layout Definitions. The Clinical Data Management System (CDMS) Database server 40 holds the real-time clinical trial data for the Information Presentation Module (IPM) and the CDMS web sites. The CDMS Web Server 50 hosts the CDMS web site and holds the Screen Layout Definitions. User computers 12 interact with TruPoints platform 10 via the Internet or an Intranet.

B. Reports Based on Real-Time Clinical Data

The virtual data room (TruPoints) provides several reports to users that convey information regarding the status of the clinical trial study. These reports are based on real-time patient clinical data provided from the CDMS database server 40 and are available only to a first set of users who have access to the virtual data room. The data may include, but need not be limited to, patient enrollment, safety and efficacy data, all presented in a manner that would not unblind the study. The first set of users is stored in the TruPoints Database Server 20, and is administered using the ICAM located in the TruPoints Web Server 30. The screen layout definitions (report specifications) for creating the first set of reports are defined in the TruPoints Web Server 30. FIG. 2 shows a sample subset of first users.

The CDMS provides a second set of reports to users who are logged in to the CDMS. These reports are also based on the same real-time patient clinical data that the first set of reports (available to the users logged in to the virtual data room) are based on. The reports available to the CDMS users provide electronic access to additional real-time patient clinical data via one or more hyperlinks. (The hyperlinks are depicted as underlined text.) These hyperlinks are not available in the first set of reports. The second set of users is stored in the CDMS Database Server 40 (FIG. 1) and is administered using a user administration module located in the CDMS Web Server 50. The screen layout definitions (report specifications) for creating the second set of reports are defined in the CDMS Web Server 50. Prior art FIG. 3 shows a sample subset of second users.

"Real-time" as used herein can be completely real-time, or there could be periodic caching of data in the CDMS database so the real-time data would include the data from the last periodic caching.

The clinical trial data is made up of a plurality of data records for each of the patients. Some data records may be repeatedly updated during the period of the clinical trial, such as the data records associated with a patient's current vital signs, or a patient's current blood level, whereas other data records are entered only once during the clinical trial (e.g., a patient's blood level after x days of treatment).

Certain data records that are created have a status of being either "cleaned" or "not cleaned." As is well-known in the clinical trial database management art, the "cleaned" data records have undergone some form or degree of data validation. A status flag is provided in the CDMS database for the data records which must be cleaned, and the status flag is changed or modified after the data record is cleaned. These status flags are known in the prior art but are conventionally used only to identify data records that need action taken to be cleaned, and not as a filter criterion for creating reports regarding the status of the clinical trial study, as described further below.

Some data records may be quickly cleaned by being run through an automated set of programmatic checks (e.g., programmed rules that examine the data record to determine if it should be accepted), whereas other data records may require that a patient's medical record be pulled and physically examined. This latter process may require a real or virtual site visit, and consequently will cause more delays than those associated with data records that undergo only automated checks.

In addition to being "cleaned" or "not cleaned," a data record or the entire clinical trial database may be "locked" or "unlocked." There are various types of locks associated with clinical trial databases and data records (e.g., interim or soft locks, hard locks, full database locks), but they all have in common the fact that the data record either is allowed to be changed by certain or all users who have access to it (unlocked) or is not allowed to be changed by certain or all users who have access to it (locked). Typically, a data record is locked after it is cleaned, and thus it is common to refer to a data record as being "cleaned and locked." However, these are usually two distinct steps.

Alternatively, data records can be designated as having been cleaned by being locked, thereby defining a one-step process with the lock functioning as a proxy for the data record being cleaned. For example, the lock may be in the form of a "soft lock," in which data records associated with a piece or subset of data is locked from further editing by the study team but can still be unlocked up until the time that the overall database is formally locked and the study data is then typically submitted to biostatisticians for analysis as part of the unblinding process discussed above.

In a first embodiment of the present invention, when a report is generated for a CDMS user and/or a virtual data room user, it always pulls the most current data from the CDMS database, regardless of whether the data is associated with data records that are cleaned or locked.

In a second embodiment of the present invention, when a report is generated for a CDMS user, it always pulls the most current data from the CDMS database, regardless of whether the data is associated with data records that are cleaned, but for a designated subset of data records, the report generated for the virtual data room only pulls data associated with "cleaned" data records from the CDMS database. The designated subset of data records that must be cleaned to be used in a report generated for the virtual data room is selected by the study sponsor or the administrator of the virtual data room.

Any of the various scenarios may exist:

1. A first subset of data records must be cleaned to be used in a virtual data room report, and a second subset of data records can be used in a virtual data room report regardless of whether the data records are cleaned or not cleaned.

2. All of the data records must be cleaned to be used in a virtual data room report. This is a special case where the subset encompasses all of the data records needed for a particular virtual data room report.

In one example of the second embodiment, the "lock" status of the data records has no bearing on whether or not the data records are used in either the CDMS or virtual data room reports. Thus, a data record must only be cleaned to be used for a virtual data room report. In another example of the second embodiment, the "lock" status is used as another filtering criterion for generating virtual data room reports, and for the designated subset of data records, only data associated with locked data records are used for generating the virtual data room reports. Thus, in this example, a data record must be cleaned and locked to be used.

A third embodiment of the present invention is similar to the second embodiment in that the virtual data room only pulls data from the CDMS database based on the "cleaned" status of the data for the designated subset of data records, but with the extra constraint related to the status of the patient in the treatment regimen, whereas no such exclusion is made in the CDMS report. For example, the virtual data room would only pull data, or a subset of data, of patients who are at a designated stage of the treatment regimen, whereas a report generated for a CDMS user would not have these restrictions. This difference is highlighted in the virtual data room report shown in FIG. 13 which includes only patients who have completed the treatment regimen (i.e., "completed patients"), compared to FIG. 12 which shows a CDMS report that is not limited to completed patients. Likewise, the virtual data room report shown in FIG. 4 includes only "completed" patients (CRF status=C), whereas related CDMS reports are not necessarily limited in this manner. See, for example, the query preview filter in FIG. 10 which allows the CDMS user to select patients with a status other than "completed." Again, a status flag is provided in the CDMS database for the patient status, and this flag must be set to "completed" for patient data to be shown in a virtual data room report. The status of being a "completed" patient is protocol-specific (i.e., it depends upon the clinical trial protocol), as is well-known in the art. Also, "completed" may refer to completed all treatment, completed one cohort, completed one doctors visit or the like. FIGS. 4, 10, 12 and 13 are discussed in more detail below.

Figure 13:

The second embodiment described above allows the virtual data room to avoid exposing unvalidated/unchecked data to users who are not actually running the clinical trial. While it may be acceptable for a CDMS user to see reports that may contain unvalidated/unchecked data, a clinical trial sponsor would not likely want to allow potential investors and potential licensees to view reports having certain unvalidated/unchecked data, such as adverse event/safety data (FIG. 4) or unvalidated/unchecked patient symptom data (FIG. 13). In contrast to these types of data, certain less critical data such as patient enrollment data (e.g., the number of patients currently enrolled in the study) may be acceptable to show to virtual data room users, even if it is not cleaned. Regarding the third embodiment, a similar scenario may exist for patients who have not reached a certain designated status in the treatment regimen, such as "completed."

Figure 65:
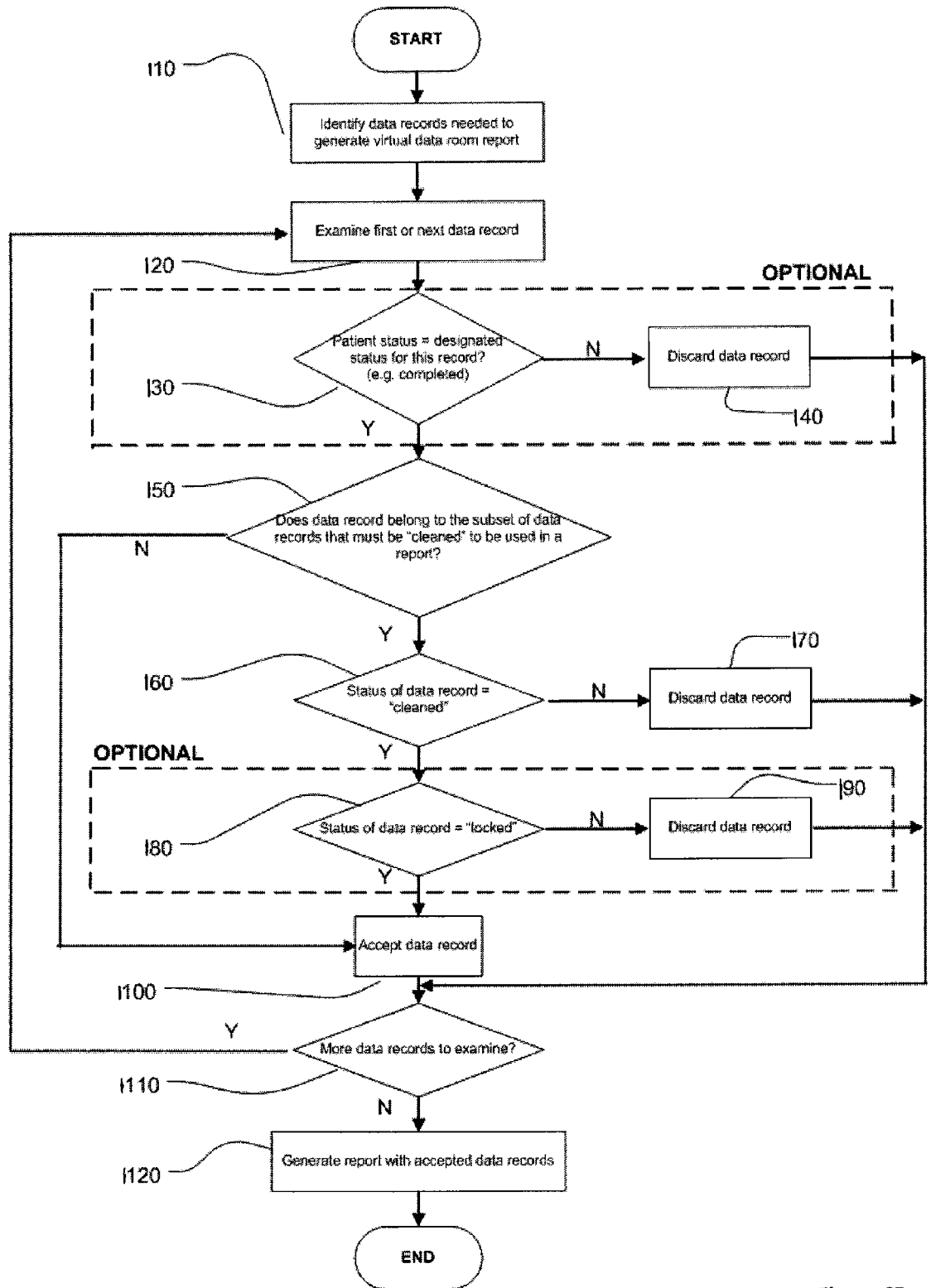
FIG. 65 is a flowchart for selecting data to be used to generate reports for the virtual data room in accordance with preferred embodiments of the present invention.

FIG. 65 is a flowchart of one preferred embodiment for selecting data to be used to generate reports for the virtual data room in accordance with the second and third embodiments of the present invention described above. The data records needed to generate the desired virtual data room report are identified (step 110) and the first data record is examined (step 120). The patient status is optionally checked (step 130), and if the patient status is not in a designated status (e.g., "completed"), the data record is discarded (step 140) and the next data record is examined (steps 1110 and 120). If the optional patient status check is performed and the patient status is in a designated status, or if the optional step 130 is skipped, then the data record is checked to see if it belongs to a predefined subset of data records that must be "cleaned" to be used in a virtual data room report (step 150). If not, then the data record is accepted (step 1100) and the next data record is examined (steps 1110 and 120). If so, then the status of the data record is checked to determine if it is cleaned (step 160). If the data record is not cleaned, then the data record is discarded (step 170) and the next data record is examined (steps 1110 and 120). The status of the data record is then optionally checked to see if it is locked (step 180). If not (i.e., data record is unlocked), then the data record is discarded (step 190) and the next data record is examined (steps 1110 and 120). If so, or if the optional step 180 is skipped, then the data record is accepted and the next data record is examined (steps 1110 and 120). If there are no more data records to examine, then a report is generated using the accepted data records (steps 1110 and 1120). Otherwise, the next data record is examined (step 120).

Figure 7:
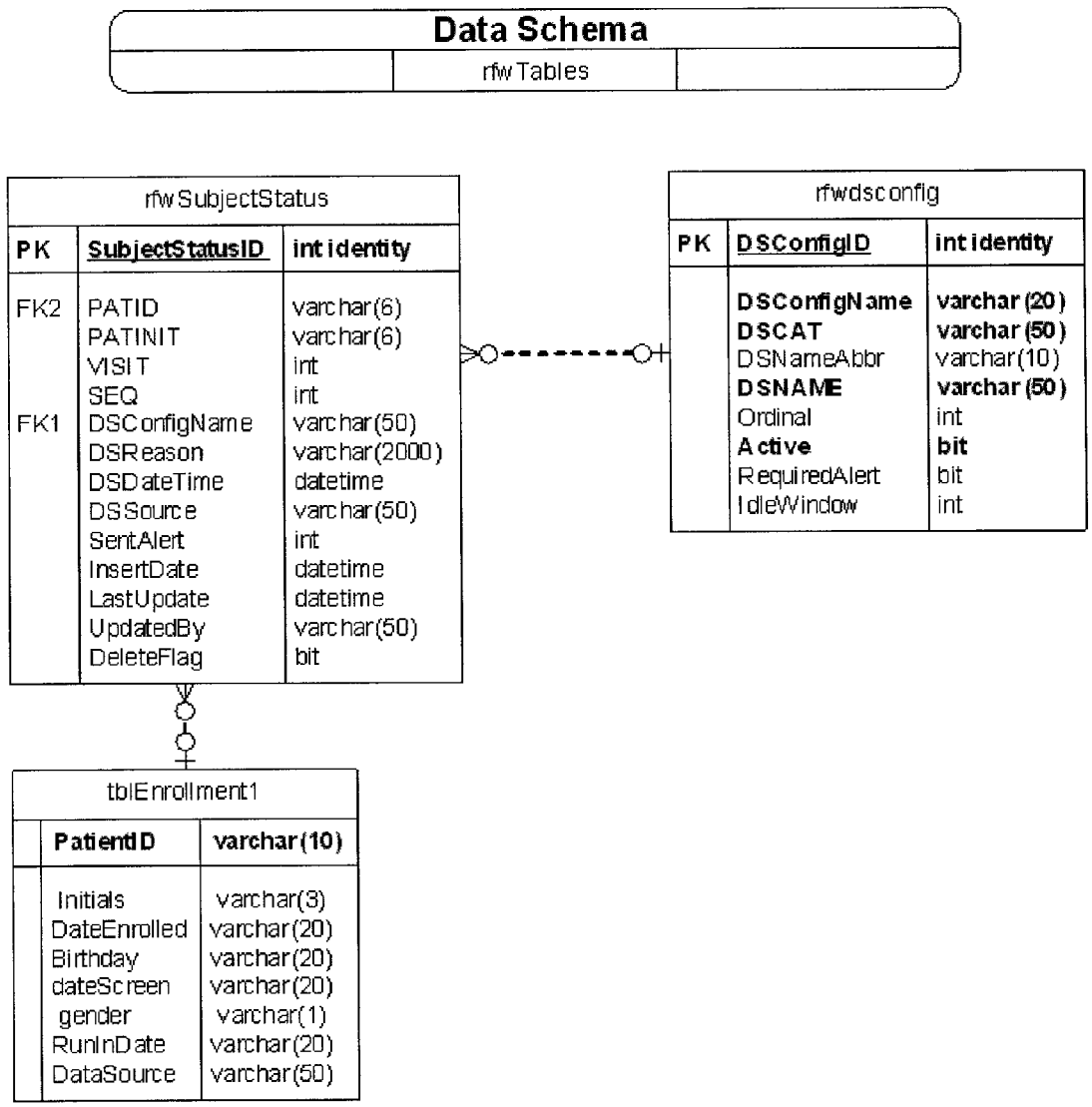

Examples of some of the real-time clinical reports that can be generated and viewed by a logged in TruPoints user and a logged in CDMS user are as follows:

1. Safety Data Summary a. The virtual data room provides the safety data summary report shown in FIG. 4. This report is displayed based on the screen layout definitions (report specifications) in FIG. 5 and Part 16 of the Appendix. The screen layout definitions are defined in the TruPoints web server 30 (FIG. 1). This report is generated based on the SQL query in Part 1 of the Appendix. SQL schemas for the tables and views used in this report are shown in prior art FIGS. 6 and 7, and prior art Parts 8, 9, 10 and 11 of the Appendix. This report does not provide any hyperlinks that enable access to additional real-time clinical patient data. The disclosed version of this report does not identify a subset of data records that must be cleaned before being used in this report and then filter out any uncleaned data records when generating the virtual data room report. However, in the second and third embodiments discussed above, these steps would occur. Specifically, at least steps 150 and 160 of FIG. 65 would be used when generating this report.

b. The CDMS provides the safety data summary report (also called AE Report (Adverse Event Report)) as shown in prior art FIG. 8. The AE report is displayed based on the screen layout definitions in prior art FIG. 9 and prior art Parts 12 and 13 of the Appendix. The SQL query to generate this report is seen in prior art Part 2 of the Appendix. SQL schemas for the tables and views used in this report are provided in FIG. 6. This report provides hyperlinks to additional screens (FIGS. 10 and 11), which display additional real-time patient clinical data. The screen shown in FIG. 10 is displayed by clicking on a hyperlink associated with the Patient ID in prior art FIG. 8. The screen shown in FIG. 11 is displayed by clicking on a hyperlink associated with the visit and eCRF Name in FIG. 10. In contrast to the safety data summary report shown in FIG. 4 implemented in accordance with the second and third embodiments, at least steps 150 and 160 of FIG. 65 are not be used when generating this report.

Figure 15:
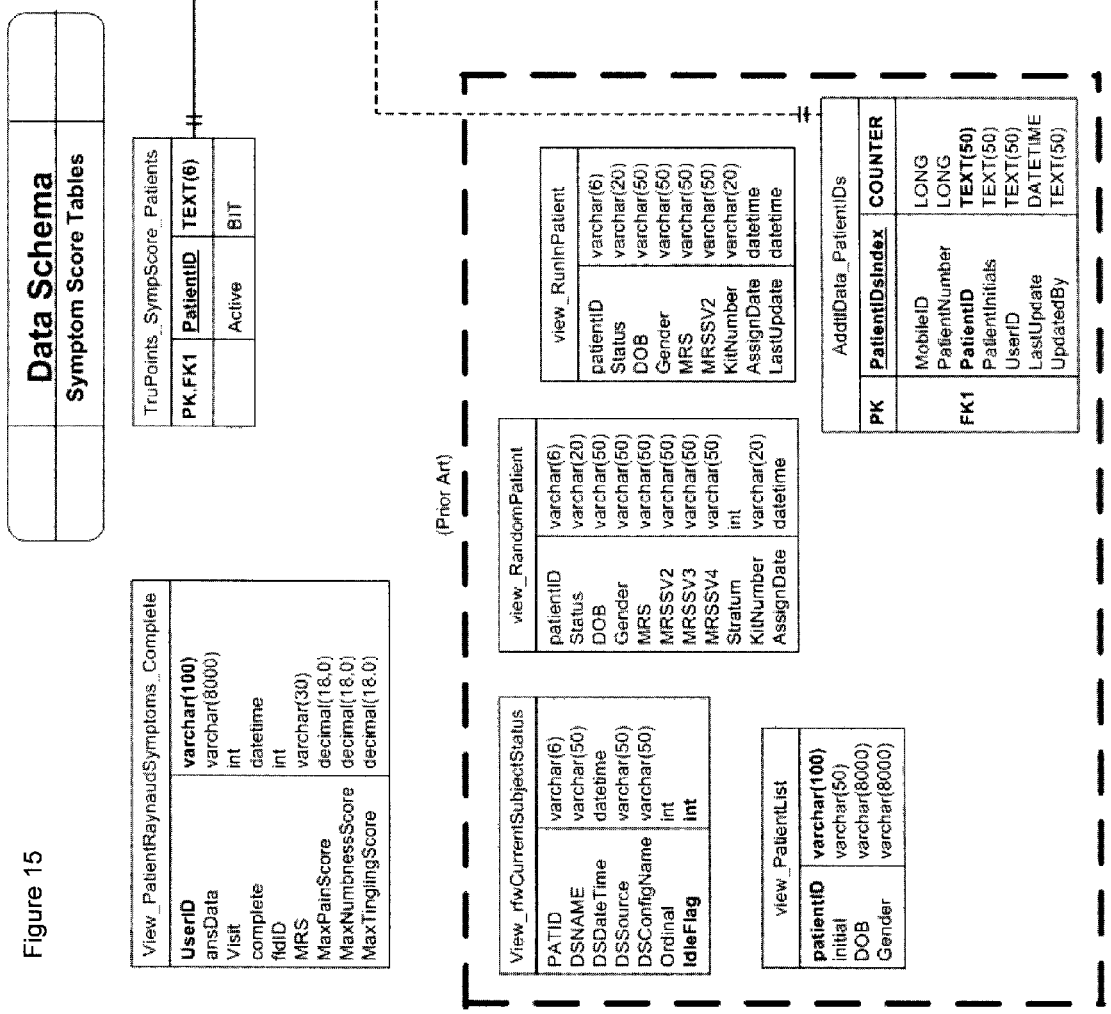
FIG. 15 shows a data schema and data tables that includes prior art and non-prior art portions.
Figure 16:
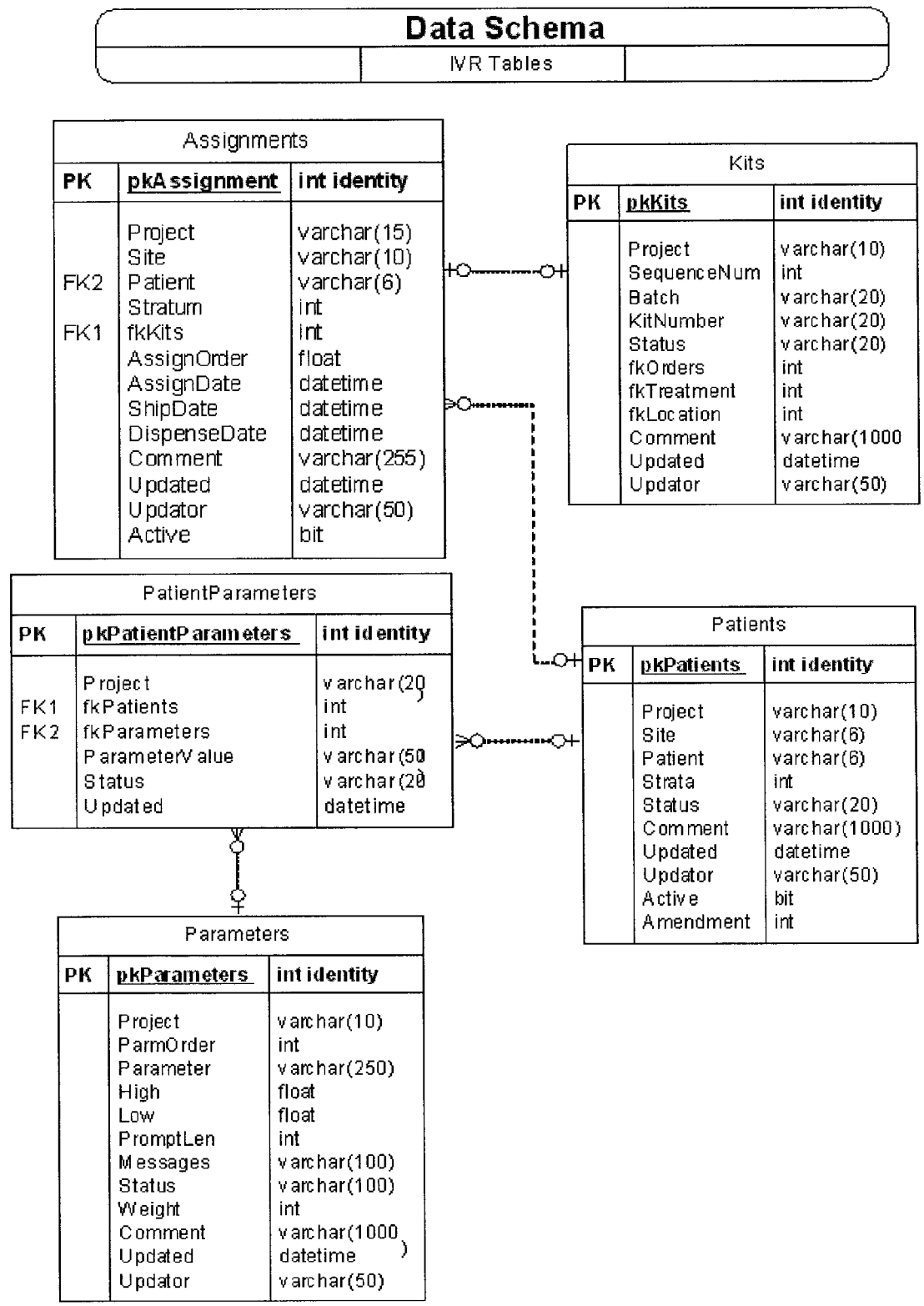
Figure 17:
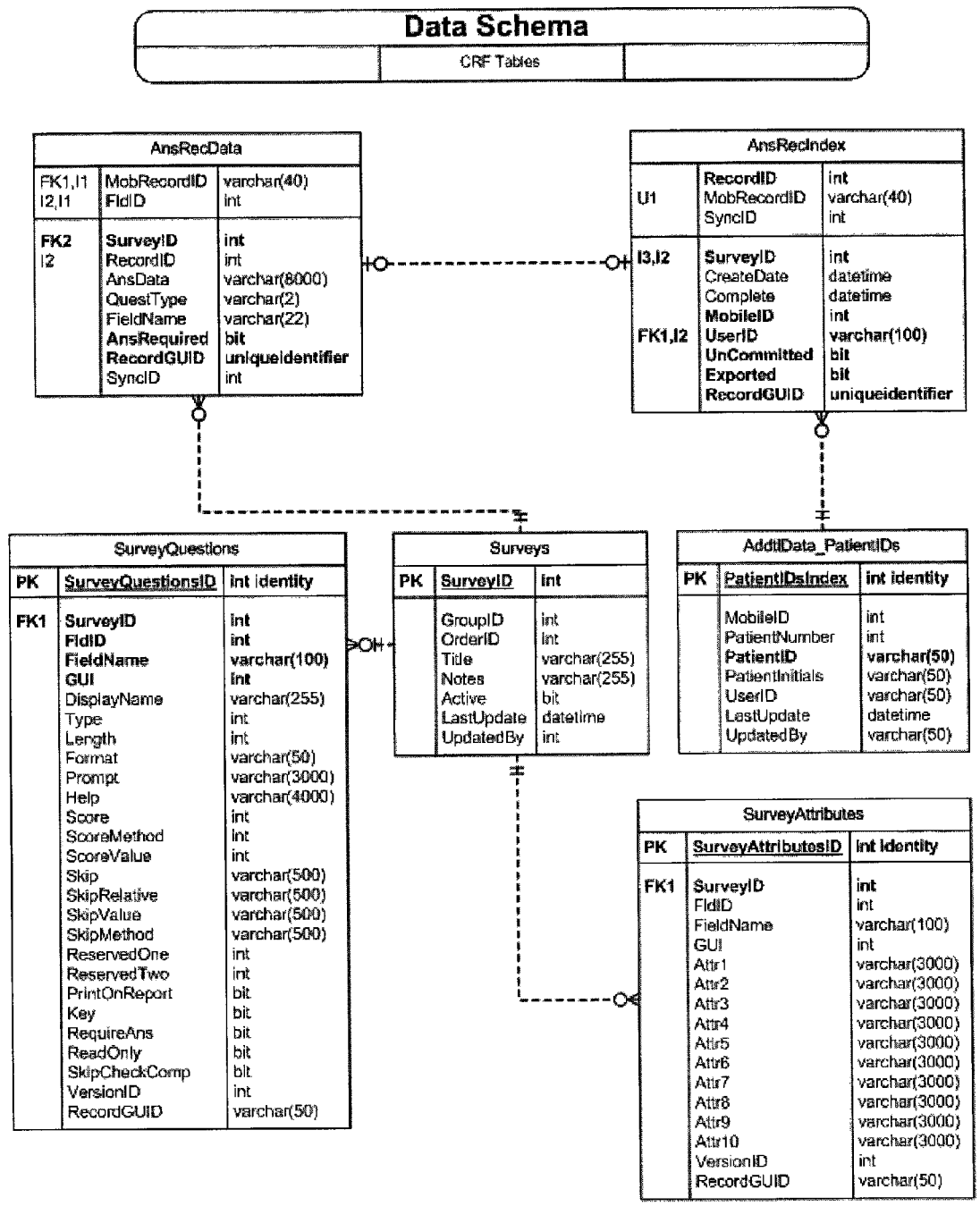

2. Symptom Score Report a. The virtual data room provides the Symptom score report shown in FIG. 13, which is one example of patient blinded efficacy data. This report is displayed based on the screen layout definitions (report specifications) in FIG. 14 and Part 14 of the Appendix. The SQL statement to generate this report is shown in Part 3 of the Appendix. SQL Schemas for the tables and views used in this report are provided in FIG. 15 (dashed portions of which are prior art) and prior art FIGS. 16 and 17, and prior art Parts 4, 5, 6, 7, 10, and 11 of the Appendix. This report does not provide any hyperlinks that enable access to additional real-time clinical patient data. A subset of data records that must be cleaned before being used in this report may be identified and then any uncleaned data records related to this subset of data records would be filtered out before generating the virtual data room report. Specifically, at least steps 150 and 160 of FIG. 65 would be used when generating this report. The table labeled "TruPoints_SympScore_Patients" in FIG. 15 is used to implement this feature wherein the Active field is used to indicate a cleaned data record. Parts 20-22 of the Appendix further illustrate one preferred embodiment for identifying and selecting only cleaned CRF data (referred to in the source code as being "complete" data) for subsequent use in the table labeled "PatientPeakScore_Complete" in FIG. 15 which, in turn, is used to create the virtual data room report.

b. The CDMS provides the Symptom score report (also called the Site supplies summary report) as shown in FIG. 12. This report is displayed based on the screen layout definition in prior art FIG. 18 and prior art Part 15 of the Appendix. The SQL statement to generate this report is shown in prior art Part 17 of the Appendix. SQL Schemas for the tables and views used in this report are provided in prior art FIGS. 7, 16, 17 and 19, and prior art Parts 4, 5, 6, 7, 8, 9, 10, 11, 18, and 19 of the Appendix. This report provides hyperlinks to additional screens (prior art FIGS. 10, 11, 20 and 21), which display additional real-time patient clinical data. The screen shown in FIG. 20 is displayed by clicking on a hyperlink associated with the V2 Qualifier in FIG. 12. The screen shown in FIG. 21 is displayed by clicking on a hyperlink associated with the Randomization in FIG. 12. The screen shown in FIG. 10 is displayed by clicking on a hyperlink associated with the Patient ID in FIG. 12. The screen shown in FIG. 11 is displayed by clicking on a hyperlink associated with the visit and eCRF Name in FIG. 10. In contrast to the symptom score report shown in FIG. 13, at least steps 150 and 160 of FIG. 65 are not be used when generating this report, nor is a "TruPoints_SympScore_Patients" table used.

C. Information Control Administration Module (ICAM)

Figure 22:
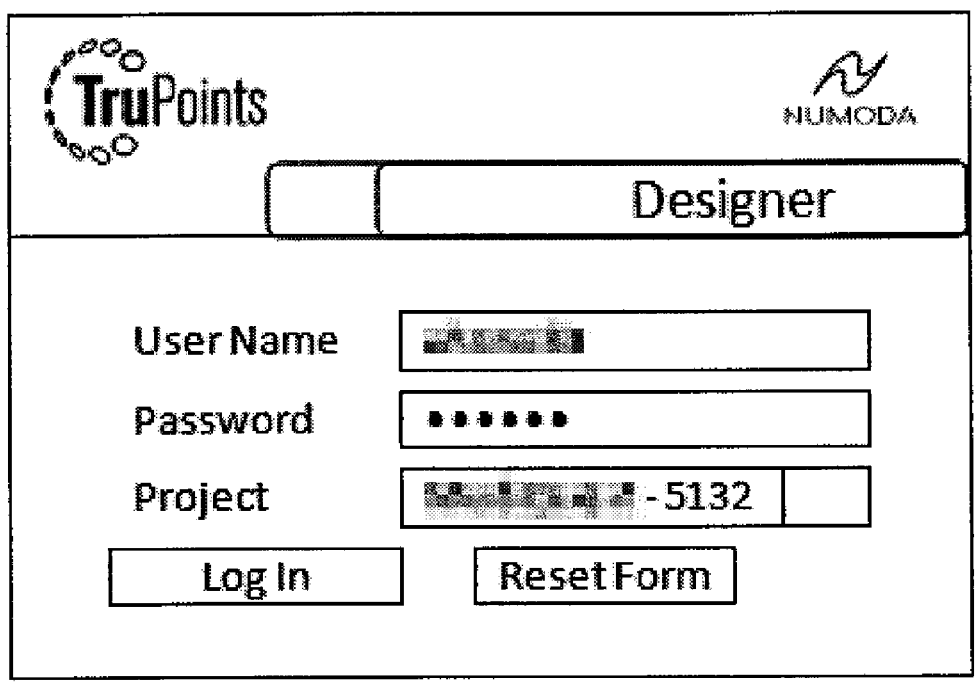

The Information Control Administration Module (ICAM) is used to specify which reports will be made available to users. Access to ICAM is controlled by a separate application called the Tracking System. In the Tracking System, usernames and passwords are assigned to Group Policies. The Group Policies are associated with Applications and access is configured accordingly. Users in the Tracking System which are assigned a Group Policy with access to the ICAM application can log into ICAM as ICAM Administrators (Admin). FIG. 22 shows the login screen for ICAM. The user enters their Tracking System username and password and then selects either one project or all projects from the project dropdown. For this example, the user has selected "XXXXXX-5132". After the ICAM Admin logs in, they are defaulted to the "Users" page (FIG. 23). Here, an ICAM Admin is able to set up a TruPoints user's login information for the Information Presentation Module (IPM).

Figure 24:
Figure 25:
Figure 29:
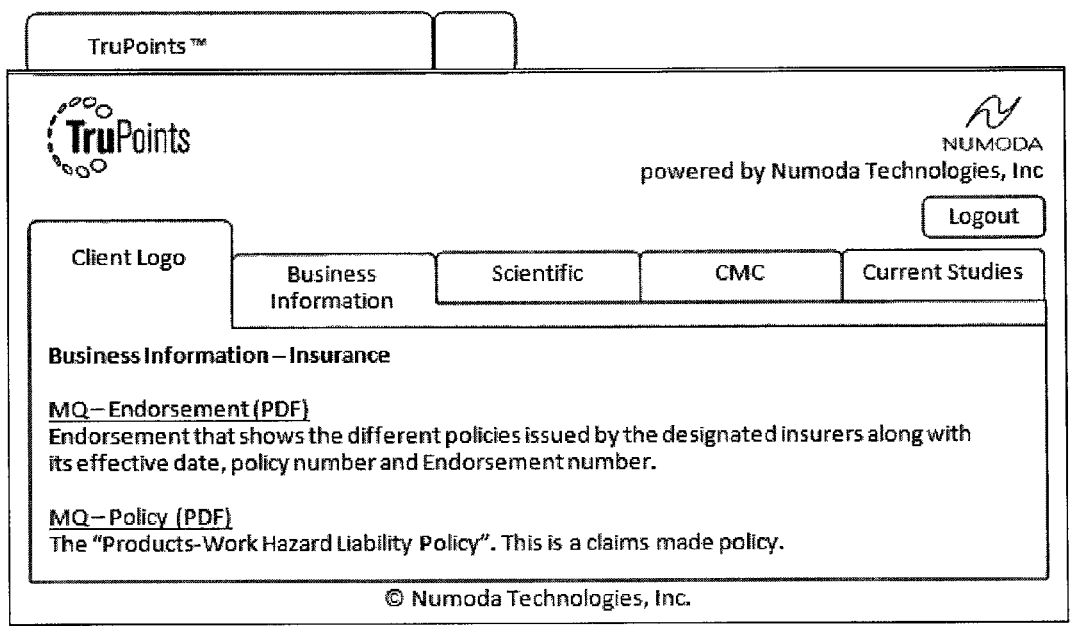
Figure 32:
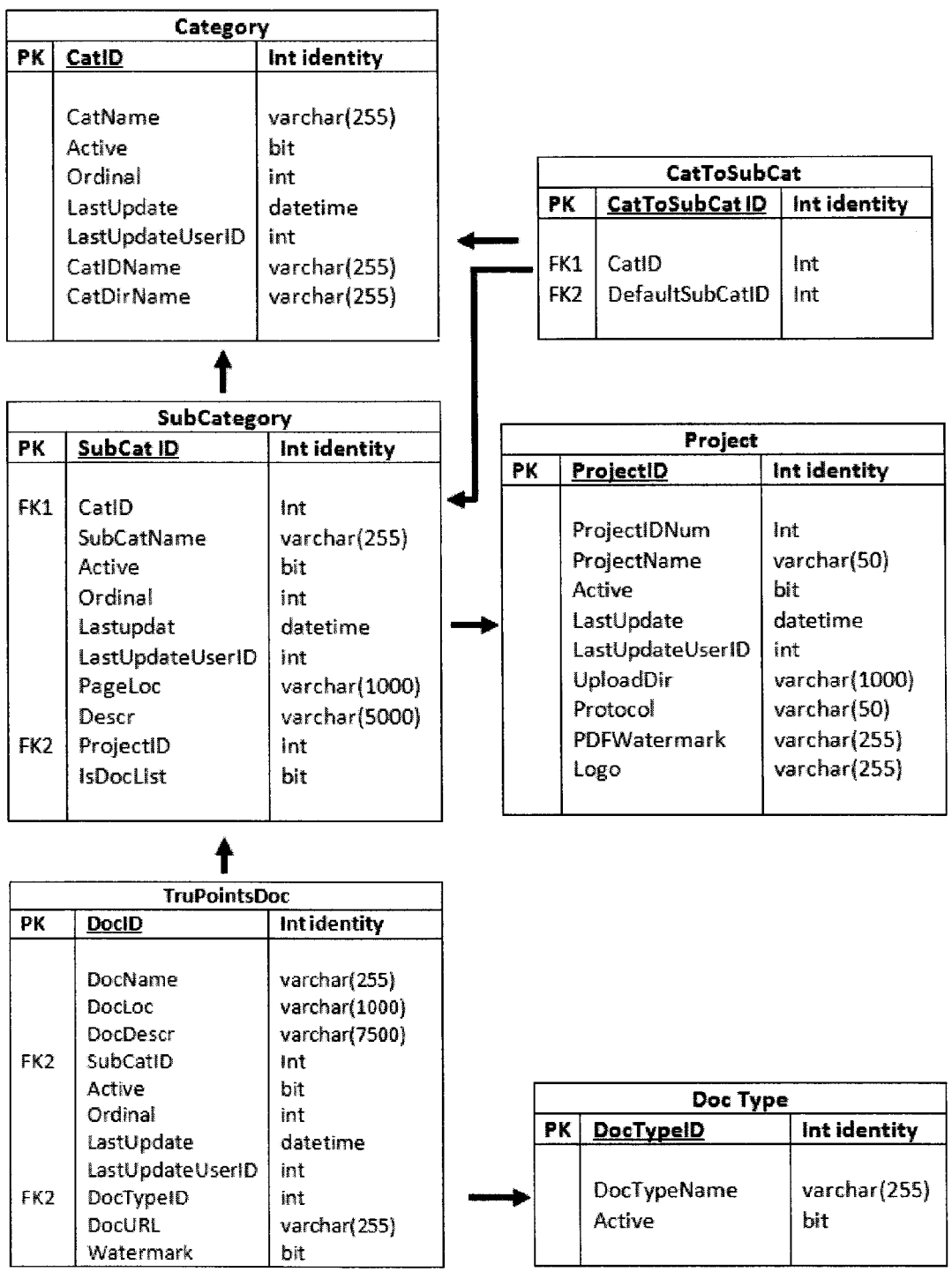

The main ICAM navigation is done first by Categories (FIG. 24 and FIG. 25), then Sub-Categories (FIG. 26, FIG. 27 and FIG. 28). The Sub-Categories are pages that the TruPoints user will see (FIGS. 29 and 30). There are two types of pages. One type of page is a list of documents associated with the clinical trial (FIG. 29). The other type of page is a report based on real-time clinical data (FIG. 30). These pages can be set to active or inactive status using the "Sub-Category"—"View/Edit" form (FIG. 31) and then selecting or clearing the "Active" check box. The database schema for the ICAM navigation is shown in FIG. 32.

To demonstrate the ICAM feature that specifies which pages can be made available to the user, the state of the "Current Studies">"Subject Status" page (FIG. 33 and FIG. 34) will be changed from active to inactive. FIG. 33 and FIG. 34 show the "Current Studies">"Subject Status" page in its active state. FIG. 33 shows the actual page and FIG. 34 shows the link to the page in the navigation pop-up menu. The ICAM Admin can make the page inactive by clearing the "Active" check box in FIG. 31 and clicking "Save". While a page's status is "Inactive," the link to it is removed from the Sub-Category links in the navigation pop-up menu. The navigation pop-up menu in FIG. 34 displays the "Subject Status" link while the "Active" check box is selected. While the Subject Status check box is not selected, the page's status is "Inactive" and the "Subject Status" link will not appear on the navigation pop-up menu (FIG. 35). The process is the same for all Sub-Categories or pages, whether they are lists of documents or reports with real-time data.

Figure 37:
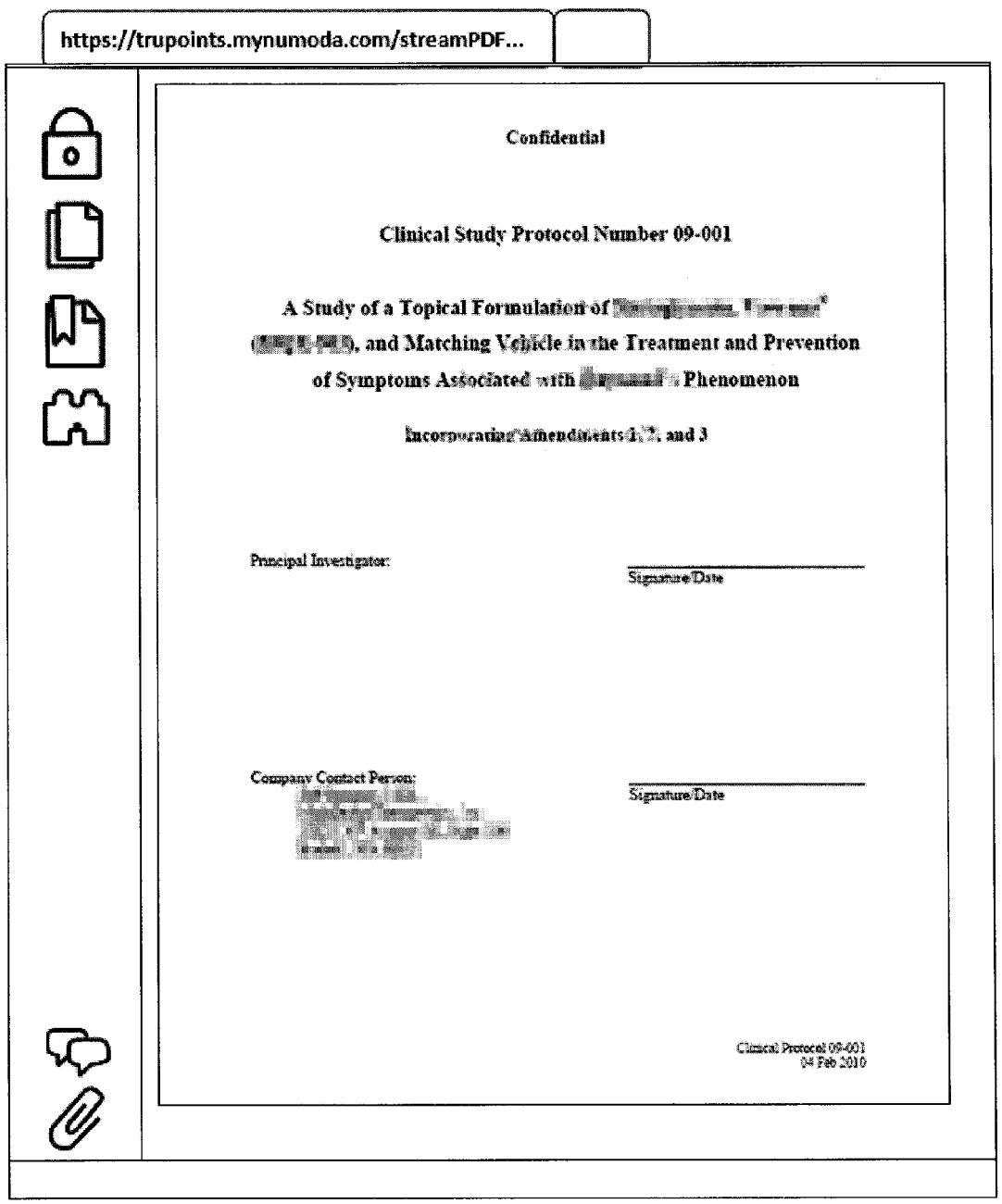

ICAM also includes a feature for specifying which documents on pages that are lists of documents will be made available to a user. For example, the "Current Studies">"Protocol 09-001" page in FIG. 36 displays a link to the "09-001 protocol with amend 3 4 Feb. 2010 (PDF)" shown in FIG. 37. In FIGS. 36 and 37, the document's status is "Active". To change the document's status to "Inactive," the ICAM Admin can use the "Documents View">"View/Edit" form (FIG. 38 and FIG. 39). The "Document View" in FIG. 38 is used by the ICAM Admin to find the documents in the IPM. After clicking the "View/Edit" link in the last column, the ICAM Admin will see the form in FIG. 39. With this form, the ICAM Admin can make the document inactive by clearing the "Active" check box and clicking "Save". While the document is inactive, the link to it is removed from the list of document links on the "Current Studies">"Protocol 09-001" page (FIG. 40). The database schema for ICAM document lists is shown in FIG. 32.

D. TruPoints Display Screens

The following list of figures identifies and describes the set of all screens seen by a user who selects every hyperlink presented by the TruPoints user interface.

Figure 41:
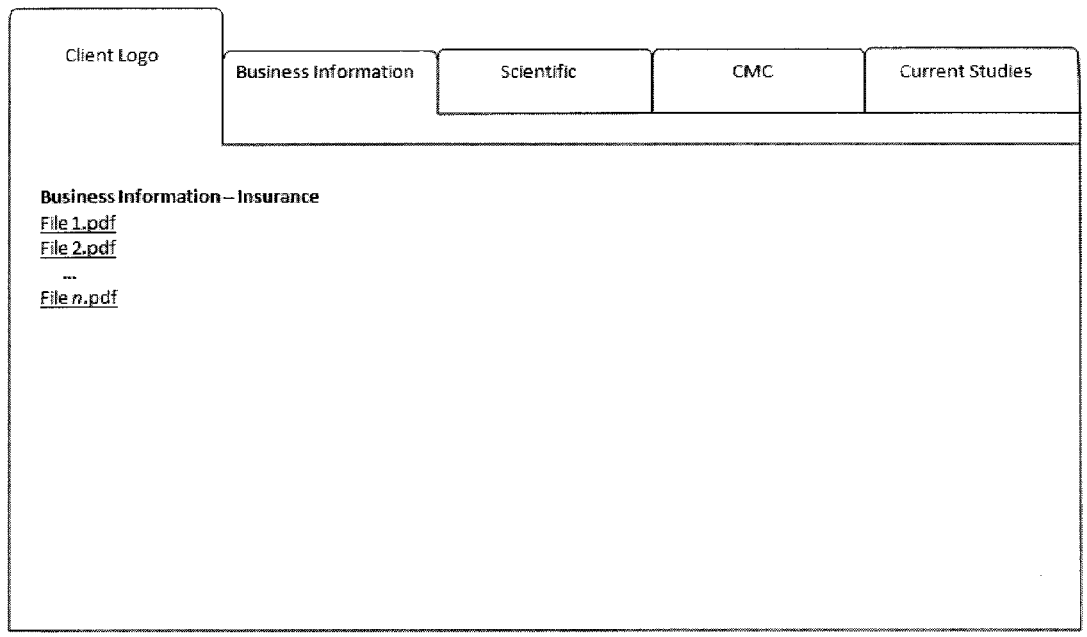
Figure 42:
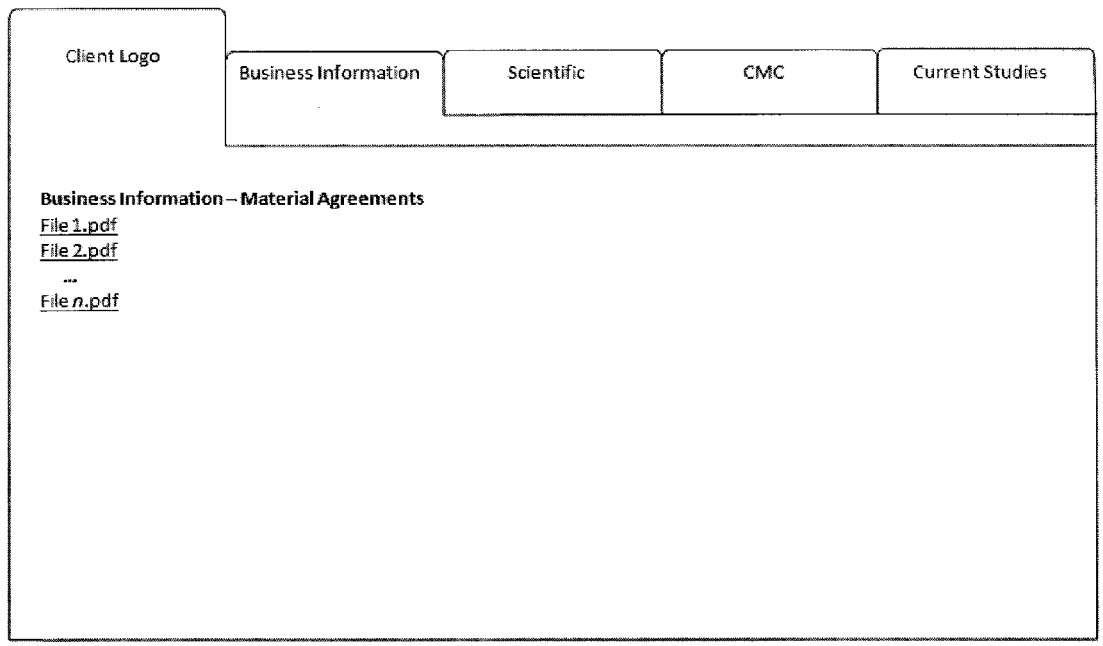
Figure 43:
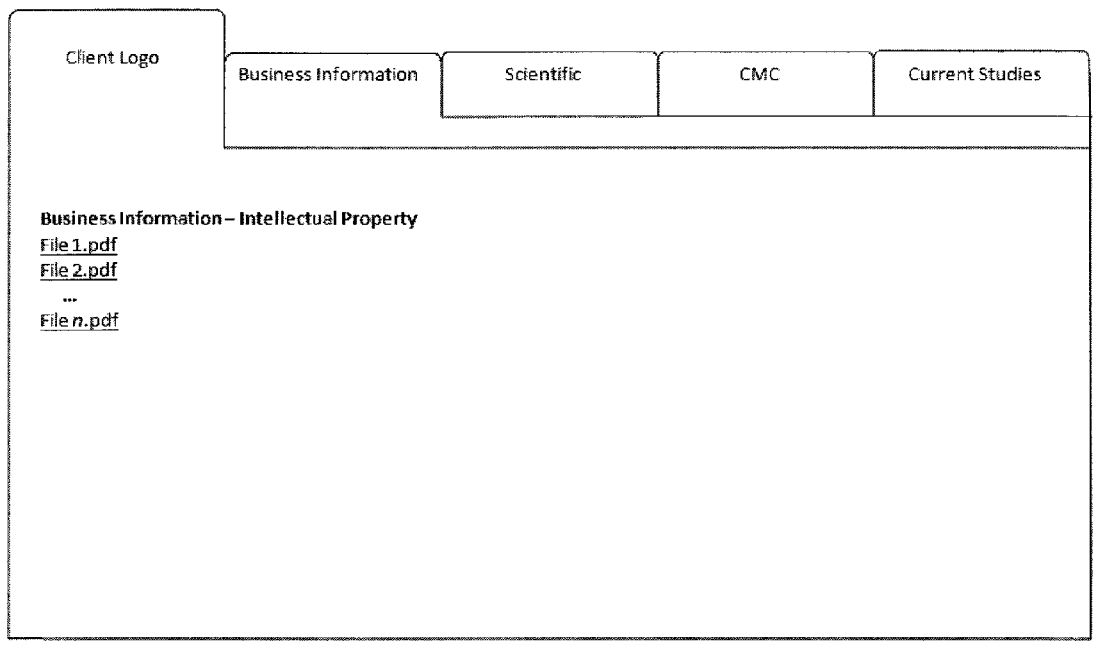
Figure 44:
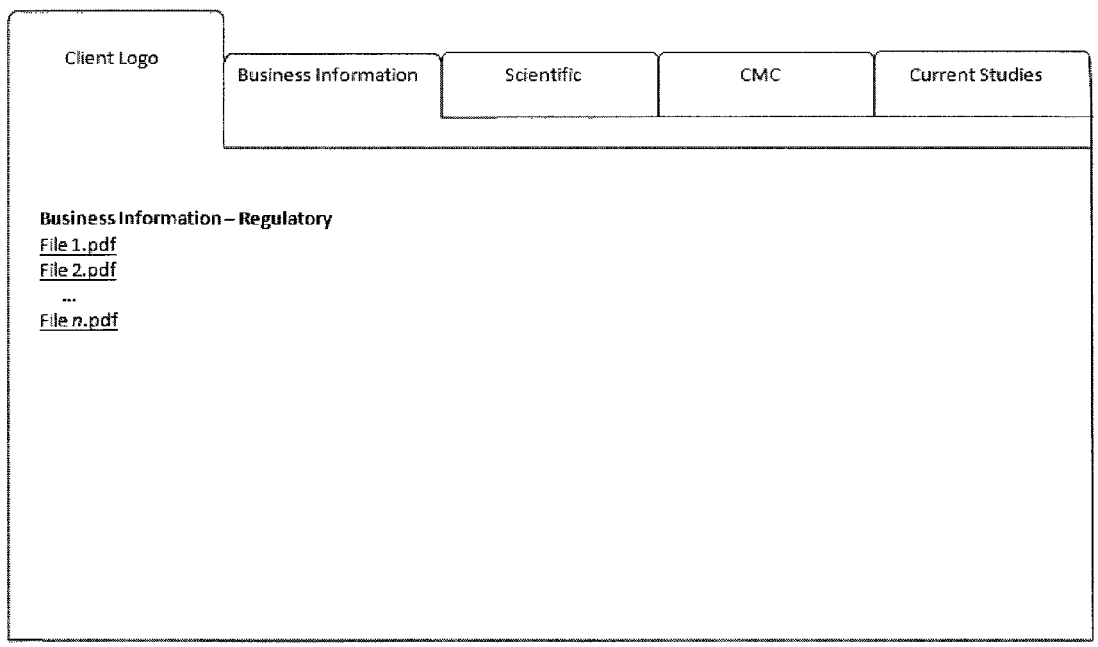
Figure 45:
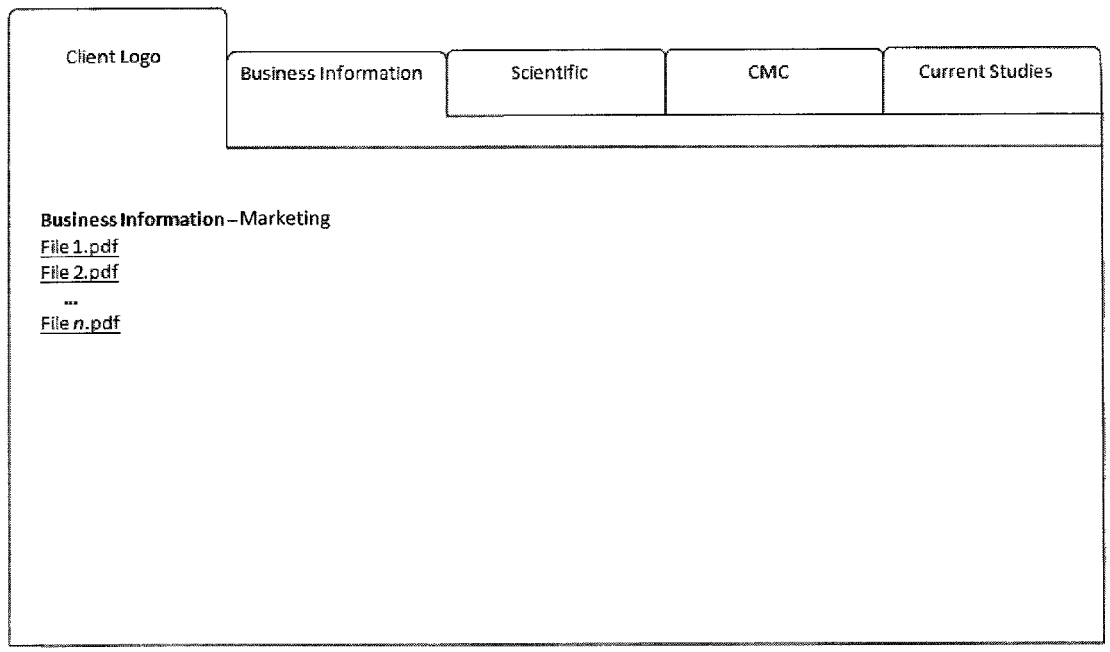
Figure 46:
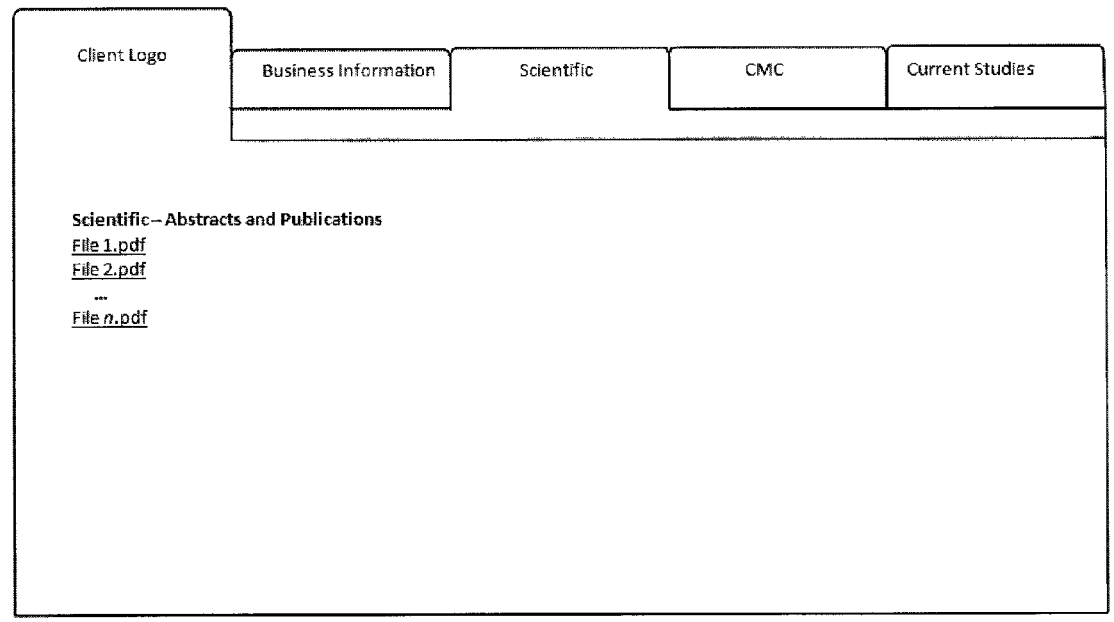
Figure 47:
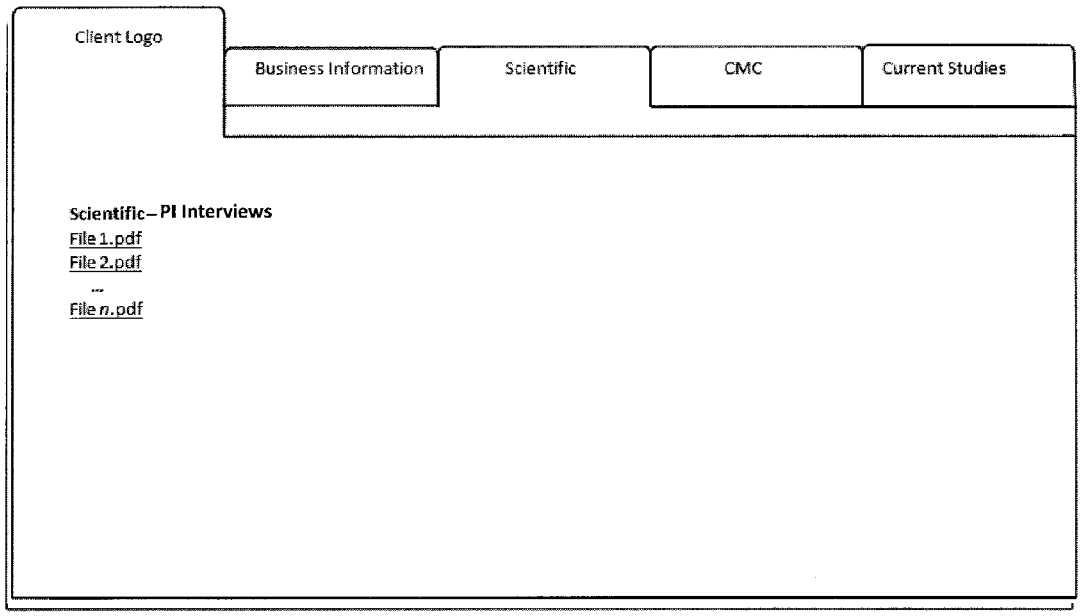
Figure 48:
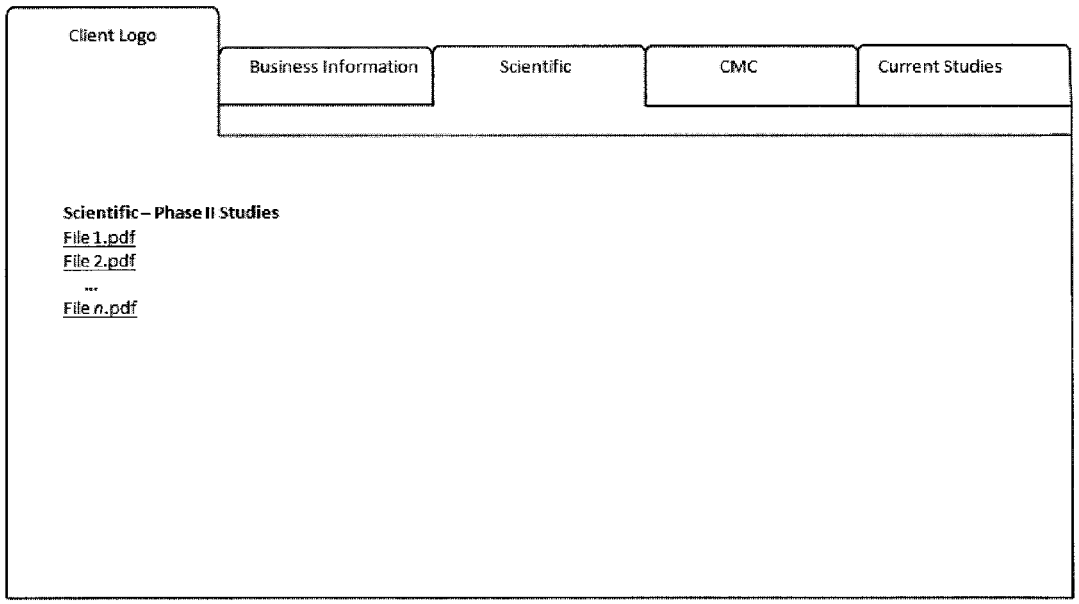
Figure 49:
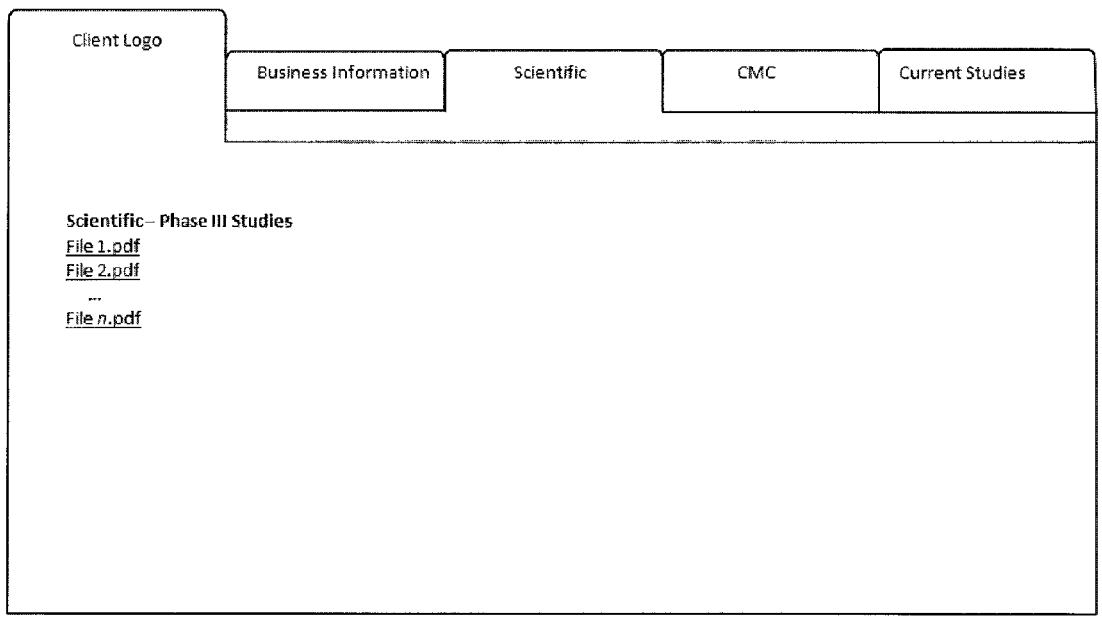
Figure 50:
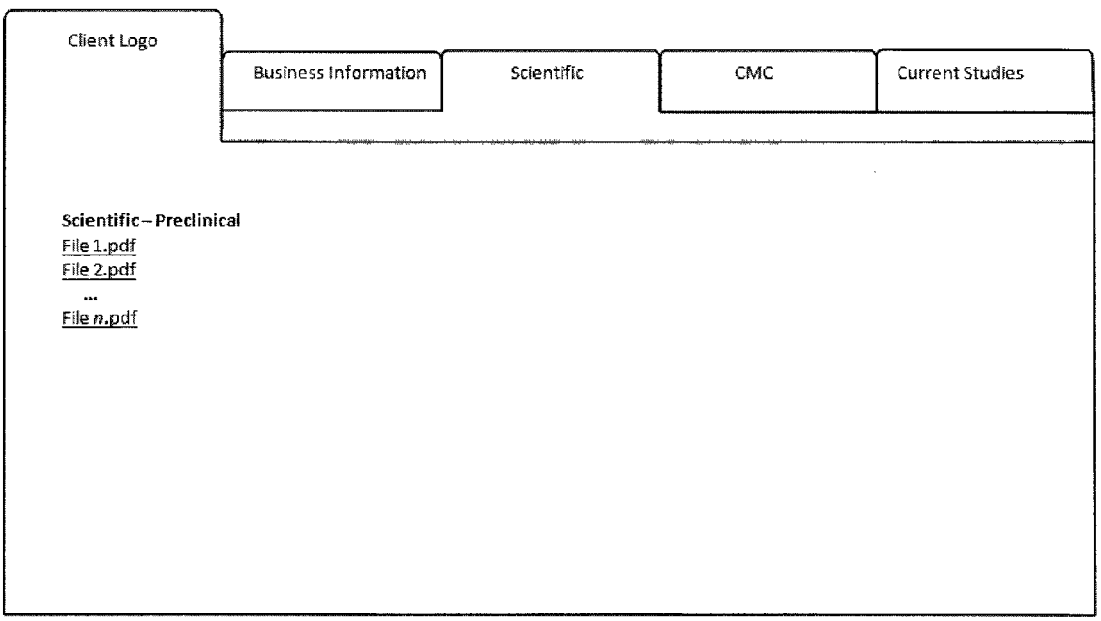
Figure 51:
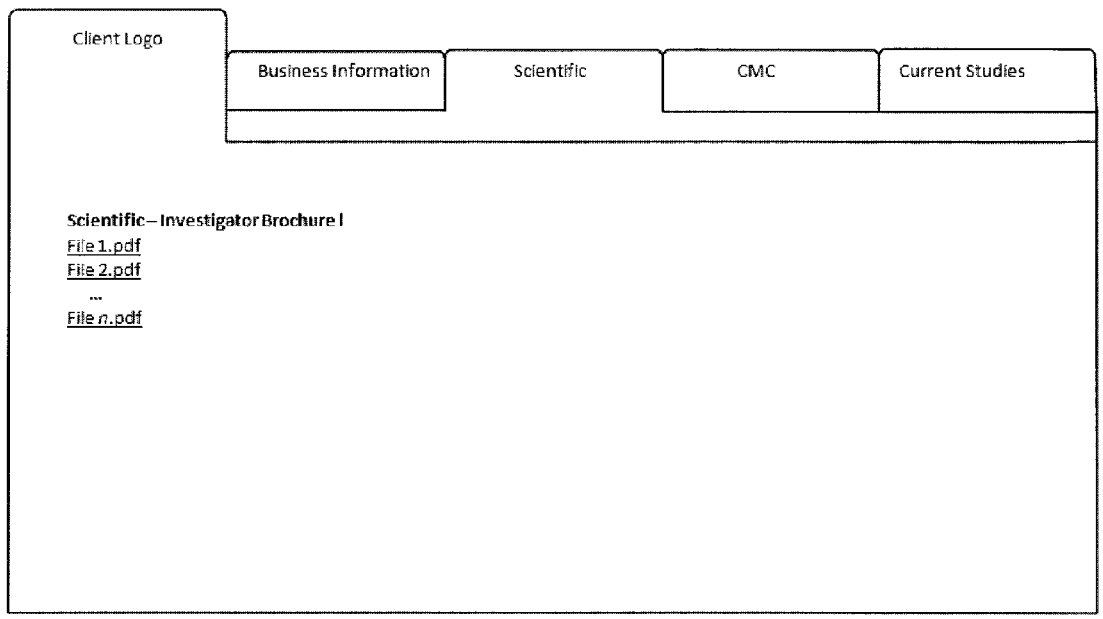
Figure 52:
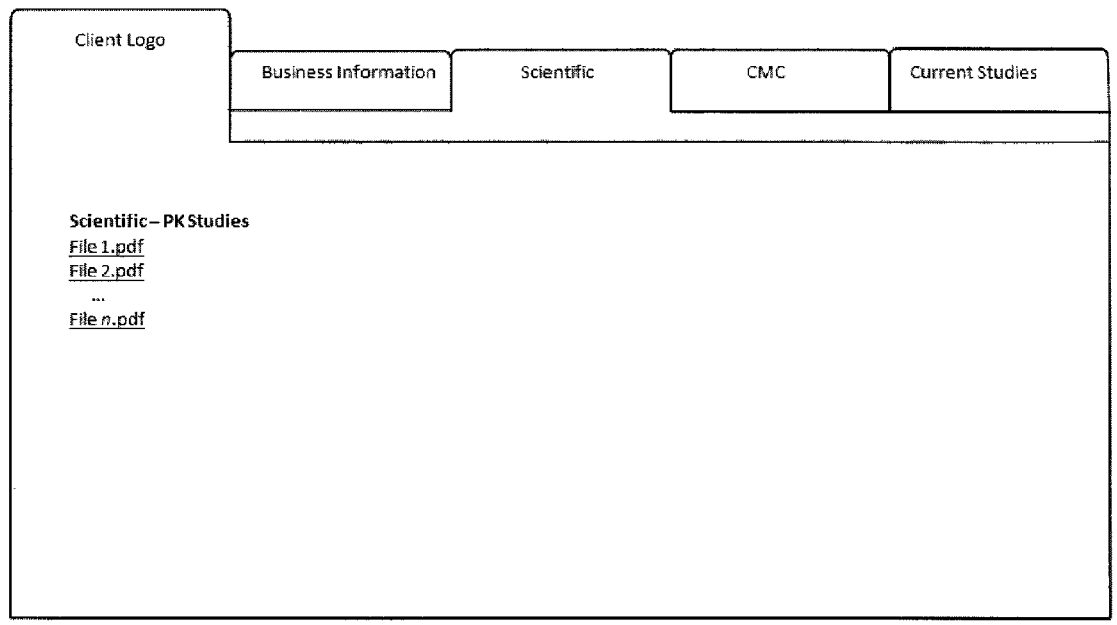
Figure 53:
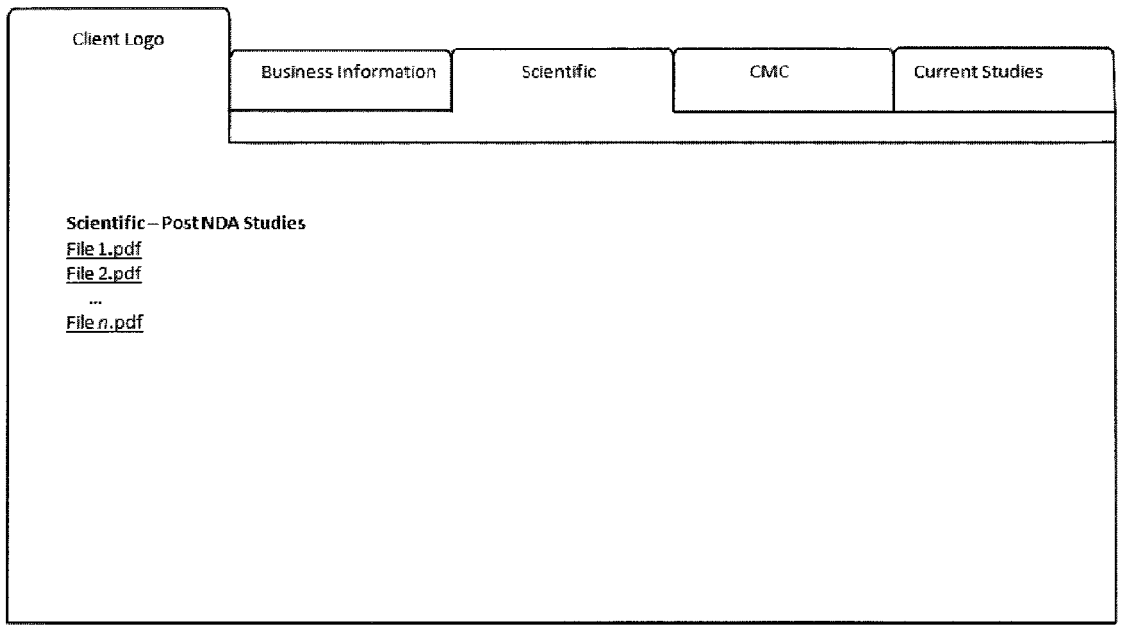
Figure 54:
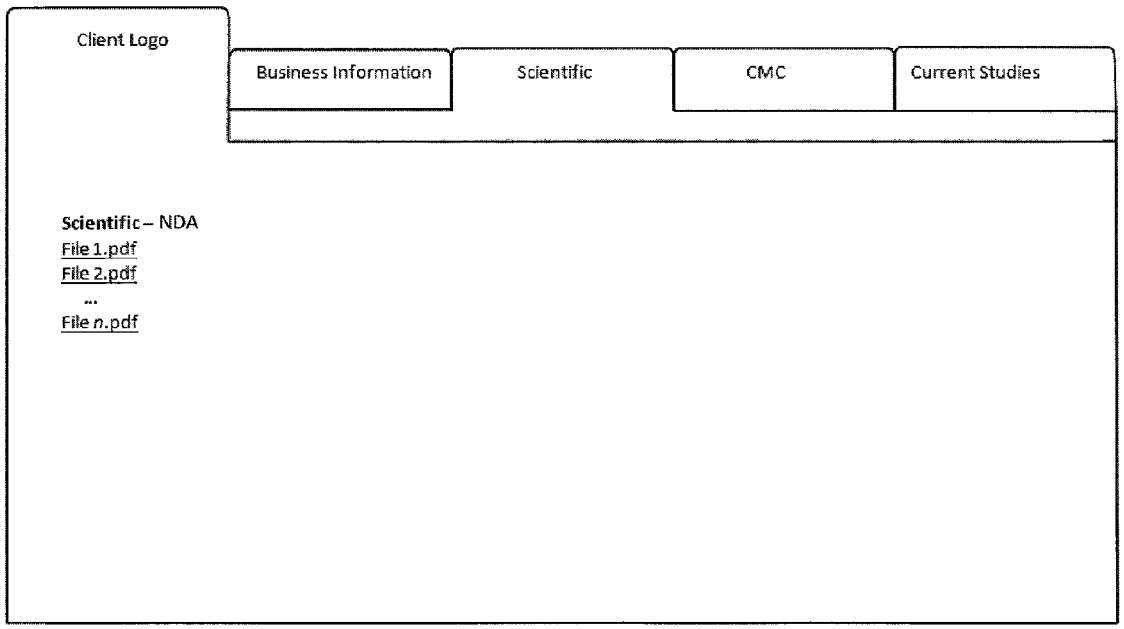
Figure 55:
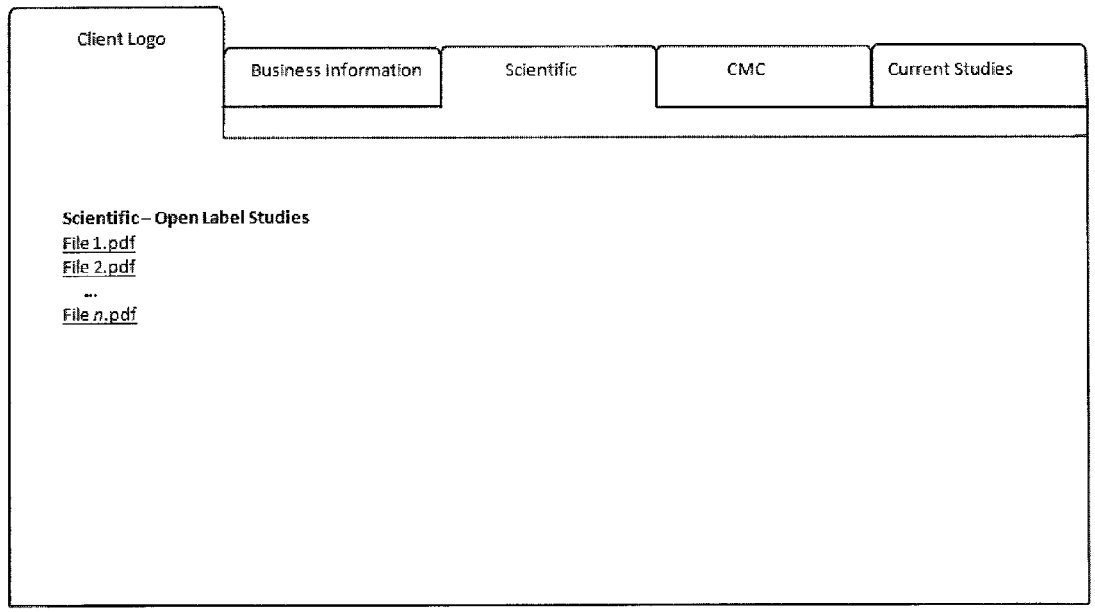
Figure 56:
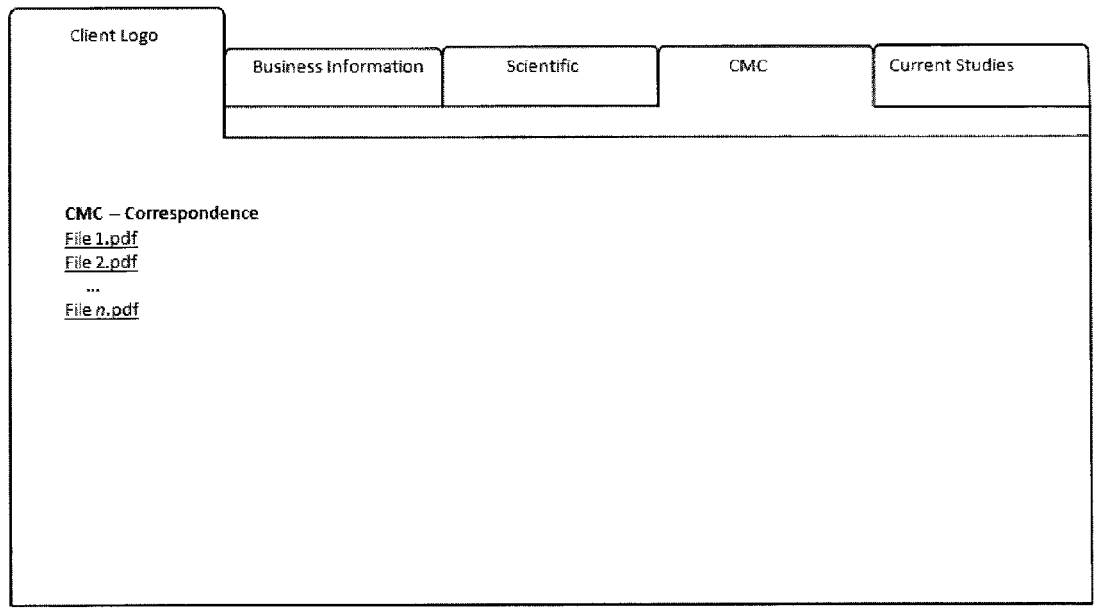
Figure 57:
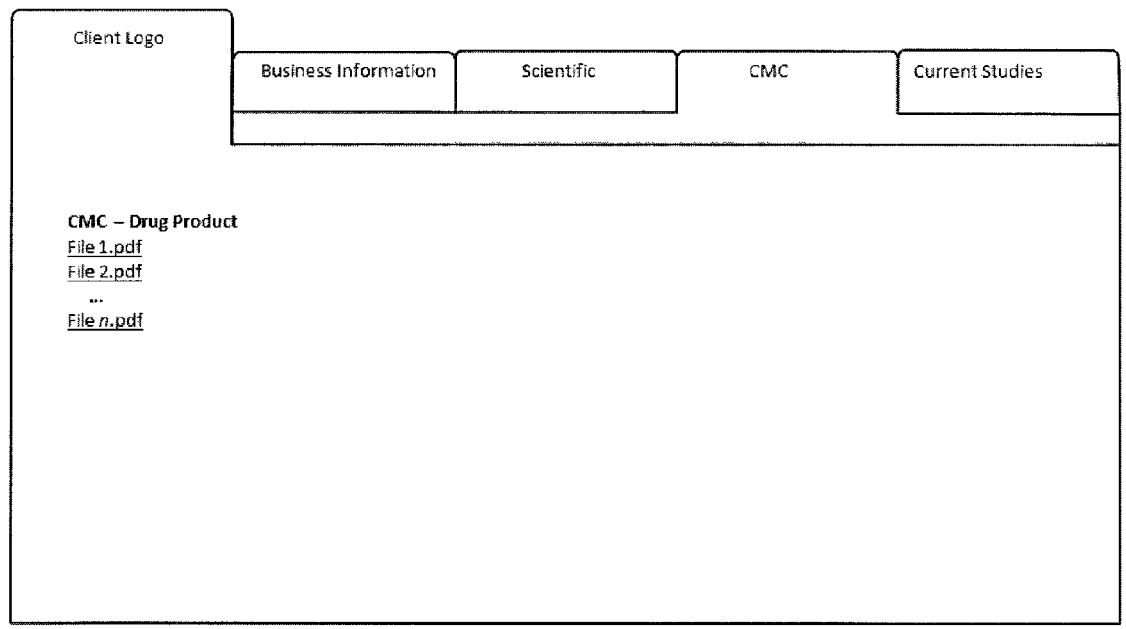
Figure 58:
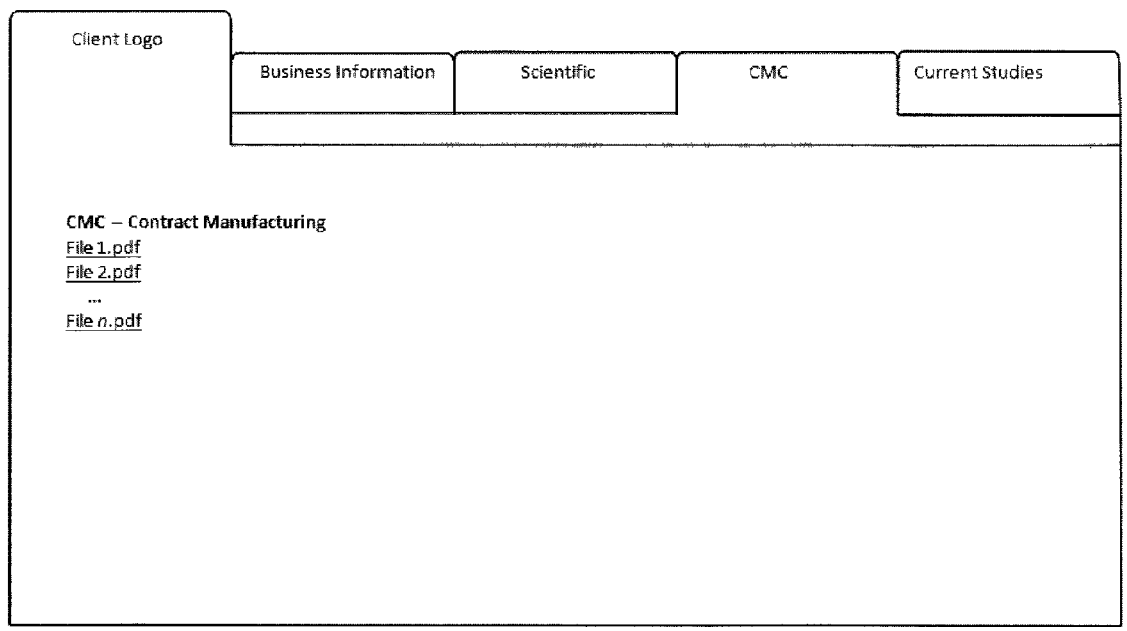
Figure 59:
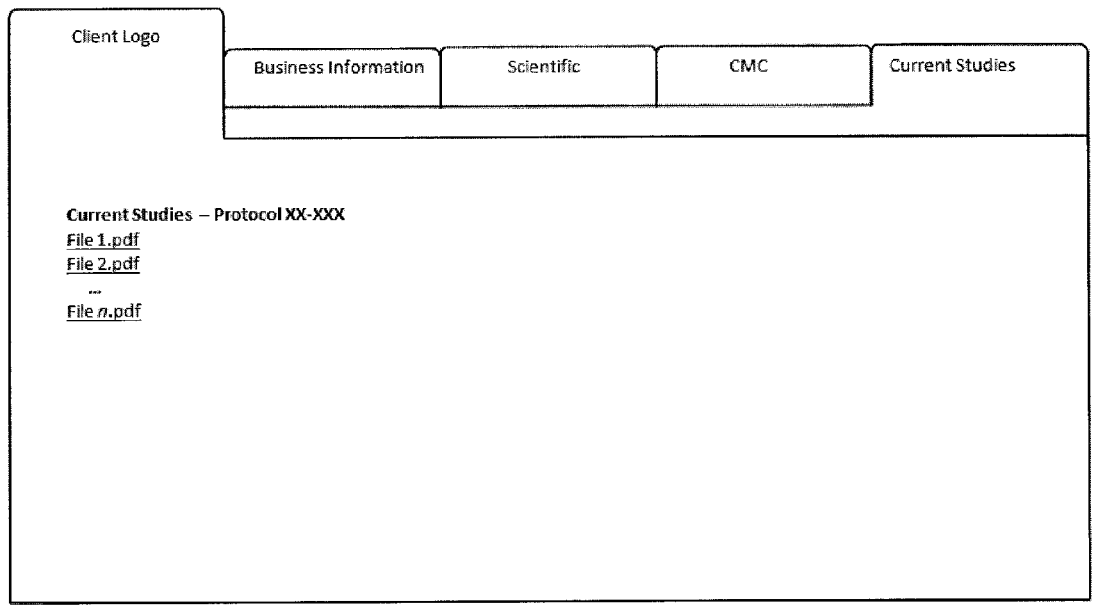
Figure 60:
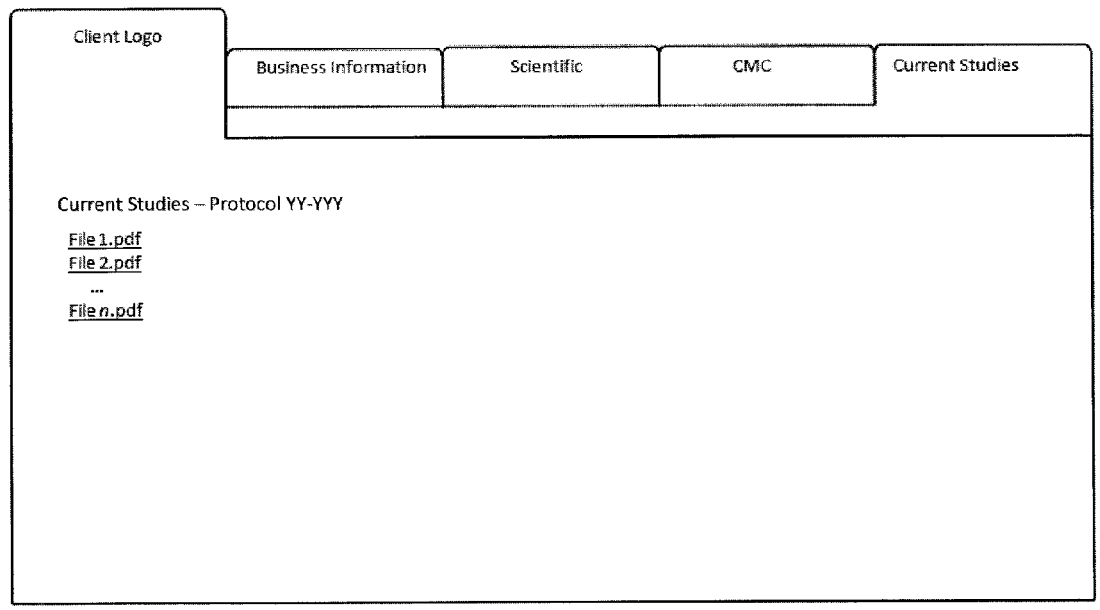

FIG. 41: Business Information tab, Insurance page
    Appears when user selects the Insurance link from the Business Information tab's menu FIG. 42: Business Information tab, Material Agreements page
    Appears when user selects the Material Agreements link from the Business Information tab's menu FIG. 43: Business Information tab, Intellectual Property page
    Appears when user selects the Intellectual Property link from the Business Information tab's menu FIG. 44: Business Information tab, Regulatory page
    Appears when user selects the Regulatory link from the Business Information tab's menu FIG. 45: Business Information tab, Marketing page
    Appears when user selects the Marketing link from the Business Information tab's menu FIG. 46: Scientific tab, Abstracts and Publications page
    Appears when user selects the Abstracts and Publications link from the Science tab's menu FIG. 47: Scientific tab, PI Interviews page
    Appears when user selects the PI Interviews link from the Science tab's menu FIG. 48: Scientific tab, Phase II Studies page
    Appears when user selects the Phase II Studies link from the Science tab's menu FIG. 49: Scientific tab, Phase III Studies page
    Appears when user selects the Phase III Studies link from the Science tab's menu FIG. 50: Scientific tab, Preclinical page
    Appears when user selects the Preclinical link from the Science tab's menu FIG. 51: Scientific tab, Investigator Brochure page
    Appears when user selects the Investigator Brochure link from the Science tab's menu FIG. 52: Scientific tab, PK Studies page
    Appears when user selects the PK Studies link from the Science tab's menu FIG. 53: Scientific tab, Post NDA Studies page
    Appears when user selects the Post NDA link from the Science tab's menu FIG. 54: Scientific tab, NDA page
    Appears when user selects the NDA link from the Science tab's menu FIG. 55: Scientific tab, Open Label Studies page
  Appears when user selects the Open Label Studies link from the Science tab's menu
FIG. 56: Business Information tab, Correspondence page
  Appears when user selects the Correspondence link from the CMC tab's menu
FIG. 57: Business Information tab, Drug Product page
  Appears when user selects the Drug Products link from the CMC tab's menu
FIG. 58: Business Information tab, Contract Manufacturing page
  Appears when user selects the Contract Manufacturing link from the CMC tab's menu
FIG. 59: Business Information tab, Protocol XX-XXX page
  Appears when user selects the Protocol XX-XXX link from the Current Studies tab's menu
FIG. 60: Business Information tab, Protocol YY-YYY page
  Appears when user selects the Protocol YY-YYY link from the Current Studies tab's menu
FIG. 61: Business Information tab, Safety Data Summary page
  Appears when user selects the Safety Data Summary link from the Current Studies tab's menu
FIG. 62: Business Information tab, Site Info page
  Appears when user selects the Site Info link from the Current Studies tab's menu
FIG. 63: Business Information tab, Site Info page
  Appears when user selects the Site Tracker Summary link from the Current Studies tab's menu
FIG. 64: Current Studies tab, Subject Status page
  Appears when user selects the Subject Status link from the Current Studies tab's menu E. Additional Items As discussed above, one preferred embodiment of the present invention is implemented via the source code in the Appendix.

In the embodiments discussed above, Numoda hosts the virtual data room and also hosts the CDMS on behalf of the entity performing the clinical trial because Numoda performs data management services for the entity that is carrying out the clinical trial. However, the scope of the invention includes embodiments wherein the host of the virtual data room has no involvement in hosting the CDMS or in performing data management services for the entity that is carrying out the clinical trial, but has electronic access to the databases that are necessary to deliver the services provided by the virtual data room. For example, an existing virtual data room service provider that currently provides conventional, static information dissemination can enhance their services by adding the ability to deliver reports based on live clinical study data of an investigational product.

The investigational product may be investigational compound (e.g., pharmaceutical drug), an investigational device, or an investigational diagnostic device, agent, or test.

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer readable media. The media has computer readable program code stored therein that is encoded with instructions for execution by a processor for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An automated method of providing data regarding the status of a clinical trial study to a first set of users who have access to a virtual data room that is used to distribute information associated with the clinical trial study, the data including real-time patient clinical data stored in a database of a clinical database management system (CDMS) associated with the clinical trial study, wherein the data includes a plurality of data records, at least some of the data records having a status of being either cleaned or not cleaned, the method comprising:
  (a) designating a subset of data records that must be in a cleaned status to be used in electronically viewable first reports regarding the status of the clinical trial study and identifying data records in the subset that have a status of being cleaned;
  (b) providing a first set of report specifications in a first memory for creating the electronically viewable first reports regarding the status of the clinical trial study for the first set of users who have access to the virtual data room, wherein for the designated subset of data records, the first set of report specifications use only real-time patient clinical data associated with the identified, cleaned data records for creating the first reports; and
  (c) automatically generating the first reports using a processor and electronically communicating the first reports to one or more of the users in the first set of users via the virtual data room.

2. The method of claim 1 wherein the data regarding the status of a clinical trial study is also provided to a second set of users who have access to the CDMS, the second set of users being different from the first set of users, the method further comprising:
  (d) providing a second set of report specifications in a second memory for creating electronically viewable second reports regarding the status of the clinical trial study for the second set of users who have access to the CDMS, wherein for the designated subset of data records, the second set of report specifications use real-time patient clinical data associated with cleaned and not cleaned data records for creating the second reports, the second set of report specifications and the corresponding second reports being different than the first set of record specifications and the corresponding first set of reports; and
  (e) automatically generating the second reports using the processor and electronically communicating the second reports to one or more of the users in the second set of users via the CDMS.

3. The method of claim 2 wherein the second reports provide electronic access to additional real-time patient clinical data that is not available in the first reports.

4. The method of claim 1 wherein the first reports include data from both cleaned and not cleaned data records, the not cleaned data records being from data records other than the designated subset of data record that must be in a cleaned status to be used in the first reports.

5. The method of claim 1 wherein each patient has a designated status within the clinical trial, and wherein the first set of report specifications use only data from patients that have a predefined designated status for creating the first reports.

6. The method of claim 1 wherein each data record has a status of being either locked or unlocked, and wherein a locked status designates a status of being cleaned, and an unlocked status designates a status of being not cleaned.

7. The method of claim 1 wherein the first reports include at least one of patient safety data and patient efficacy data.

8. A computer program product for providing data regarding the status of a clinical trial study to a first set of users who have access to a virtual data room that is used to distribute information associated with the clinical trial study, the data including real-time patient clinical data stored in a database of a clinical database management system (CDMS) associated with the clinical trial study, wherein the data includes a plurality of data records, at least some of the data records having a status of being either cleaned or not cleaned, the computer program product comprising computer-readable media stored with instructions for execution by a processor to perform a method comprising:

(a) designating a subset of data records that must be in a cleaned status to be used in electronically viewable first reports regarding the status of the clinical trial study and identifying data records in the subset that have a status of being cleaned;

(b) providing a first set of report specifications in a first memory for creating the electronically viewable first reports regarding the status of the clinical trial study for the first set of users who have access to the virtual data room, wherein for the designated subset of data records, the first set of report specifications use only real-time patient clinical data associated with the identified, cleaned data records for creating the first reports; and (c) automatically generating the first reports using a processor and electronically communicating the first reports to one or more of the users in the first set of users via the virtual data room.

9. The computer program product of claim 8 wherein the data regarding the status of a clinical trial study is also provided to a second set of users who have access to the CDMS, the second set of users being different from the first set of users, wherein the instructions when executed by the processor perform a method further comprising:

(d) providing a second set of report specifications in a second memory for creating electronically viewable second reports regarding the status of the clinical trial study for the second set of users who have access to the CDMS, wherein for the designated subset of data records, the second set of report specifications use real-time patient clinical data associated with cleaned and not cleaned data records for creating the second reports, the second set of report specifications and the corresponding second reports being different than the first set of record specifications and the corresponding first set of reports; and (e) automatically generating the second reports using the processor and electronically communicating the second reports to one or more of the users in the second set of users via the CDMS.

10. The computer program product of claim 9 wherein the second reports provide electronic access to additional real-time patient clinical data that is not available in the first reports.

11. The computer program product of claim 8 wherein the first reports include data from both cleaned and not cleaned data records, the not cleaned data records being from data records other than the designated subset of data record that must be in a cleaned status to be used in the first reports.

12. The computer program product of claim 8 wherein each patient has a designated status within the clinical trial, and wherein the first set of report specifications use only data from patients that have a predefined designated status for creating the first reports.

13. The computer program product of claim 8 wherein each data record has a status of being either locked or unlocked, and wherein a locked status designates a status of being cleaned, and an unlocked status designates a status of being not cleaned.

14. The computer program product of claim 8 wherein the first reports include at least one of patient safety data and patient efficacy data.

15. A system for use in distributing information associated with an investigational product, the information including (i) electronic documents associated with the investigational product, and (ii) electronic reports based on real-time patient clinical study data of the investigational product, the system comprising:

(a) a database that includes the electronic documents; and (b) a virtual data room that is in electronic communication with the database, the virtual data room including a memory that stores the electronic reports, the real-time patient clinical study data including cleaned and not cleaned data records, and wherein for a designated subset of data records, the electronic reports use data associated with only cleaned data records, and for the remaining data records, the electronic reports use data regardless of whether the data is associated with cleaned or not cleaned data records.

16. The system of claim 15 wherein the investigational product is a pharmaceutical drug.

17. The system of claim 15 wherein each patient in the clinical study has a designated status within the clinical trial, and wherein the reports use only data from patients that have a predefined designated status.

18. The system of claim 15 wherein each data record has a status of being either locked or unlocked, and wherein a locked status designates a status of being cleaned, and an unlocked status designates a status of being not cleaned.

19. The system of claim 15 wherein the reports include at least one of patient safety data and patient efficacy data.

20. The system of claim 15 wherein the reports include data from both cleaned and not cleaned data records, the not cleaned data records being from data records other than the designated subset of data records associated with only cleaned data records.

* * * * *